(12) United States Patent
Aoki et al.

(10) Patent No.: US 11,653,820 B2
(45) Date of Patent: May 23, 2023

(54) IN-BODY IMAGE CAPTURING DEVICE AND IN-BODY MONITORING CAMERA SYSTEM

(71) Applicant: Sharp Kabushiki Kaisha, Sakai (JP)

(72) Inventors: Hitoshi Aoki, Sakai (JP); Toshihisa Gotoh, Sakai (JP); Kei Urakawa, Sakai (JP); Kishoh Takamatsu, Sakai (JP); Tomohiro Konishi, Sakai (JP); Tsuguhisa Inoue, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 120 days.

(21) Appl. No.: 17/373,875

(22) Filed: Jul. 13, 2021

(65) Prior Publication Data

US 2021/0338068 A1    Nov. 4, 2021

Related U.S. Application Data

(63) Continuation of application No. 15/735,643, filed as application No. PCT/JP2016/070049 on Jul. 6, 2016, now abandoned.

(30) Foreign Application Priority Data

Jul. 10, 2015    (JP) ................................. 2015-139241

(51) Int. Cl.
*A61B 1/00*    (2006.01)
*A61B 1/04*    (2006.01)
*A61B 1/313*    (2006.01)
*A61B 90/00*    (2016.01)
(Continued)

(52) U.S. Cl.
CPC ...... *A61B 1/00147* (2013.01); *A61B 1/00018* (2013.01); *A61B 1/00135* (2013.01); *A61B 1/041* (2013.01); *A61B 1/051* (2013.01); *A61B 1/3132* (2013.01); *A61B 17/29* (2013.01); *A61B 90/361* (2016.02); *A61B 1/00027* (2013.01); *A61B 1/00045* (2013.01); *A61B 90/37* (2016.02)

(58) Field of Classification Search
CPC ............ A61B 1/00147; A61B 1/00018; A61B 1/00027
See application file for complete search history.

(56) References Cited

U.S. PATENT DOCUMENTS 5,871,440 A  *  2/1999  Okada ................ A61B 1/00096
                                                    600/176
2003/0107652 A1* 6/2003  Williams ............. A61B 1/0684
                                                    348/E5.025
(Continued)

OTHER PUBLICATIONS

Aoki et al., "In-Body Image Capturing Device and In-Body Monitoring Camera System", U.S. Appl. No. 15/735,643, filed Dec. 12, 2017.

*Primary Examiner* — John P Leubecker
*Assistant Examiner* — Jae Woo
(74) *Attorney, Agent, or Firm* — Keating & Bennett, LLP

(57) ABSTRACT

An in-body image capturing device (camera unit) with high reliability is suggested. A camera unit (11) includes an image capturing unit that includes a lens (26) and a first illumination unit (27a) and is capable of being introduced into a body. The first illumination unit (27a) and the image capturing unit are housed in a casing (22) that is integrally molded with an integral light-transmitting body (22x) and an integral light shielding body (22y).

15 Claims, 25 Drawing Sheets

(51) Int. Cl.
*A61B 1/05* (2006.01)
*A61B 17/29* (2006.01)

(56) References Cited

U.S. PATENT DOCUMENTS

| | | | | |
|---|---|---|---|---|
| 2003/0158503 | A1* | 8/2003 | Matsumoto | A61B 1/00096 600/593 |
| 2003/0227547 | A1* | 12/2003 | Iddan | A61B 1/00096 348/E5.029 |
| 2005/0165272 | A1* | 7/2005 | Okada | A61B 1/2736 600/113 |
| 2006/0170328 | A1* | 8/2006 | Kubota | A61B 1/0676 313/495 |
| 2007/0118012 | A1* | 5/2007 | Gilad | A61B 1/273 600/109 |
| 2008/0242935 | A1* | 10/2008 | Inoue | A61B 1/07 600/176 |
| 2010/0249502 | A1* | 9/2010 | Karasawa | A61B 1/05 600/109 |
| 2013/0274554 | A1* | 10/2013 | Sato | G02B 23/2423 600/121 |
| 2016/0073855 | A1* | 3/2016 | Farr | A61B 1/0615 600/109 |
| 2016/0235282 | A1* | 8/2016 | Nakamura | A61B 1/0661 |
| 2016/0263350 | A1* | 9/2016 | Urakawa | A61B 1/0684 |
| 2017/0100086 | A1* | 4/2017 | Takasugi | A61B 5/42 |
| 2021/0093176 | A1* | 4/2021 | Kono | A61B 1/04 |

\* cited by examiner (a)

(b)

(a)

(b)

(a)

(b)

11: CAMERA UNIT
21a: FIRST GRIP PORTION
21b: SECOND GRIP PORTION
14: RECESS TYPE JOINING PORTION (a)

(b)

11: CAMERA UNIT
13: SUPPORT TUBE

IN-BODY IMAGE CAPTURING DEVICE AND IN-BODY MONITORING CAMERA SYSTEM

TECHNICAL FIELD

The present invention relates to an in-body image capturing device that is capable of being introduced into a body.

BACKGROUND ART

Endoscopic surgery is a minimally invasive surgery that performs examinations and curative treatments without a laparotomy on a patient. In endoscopic surgery, treatment instruments such as forceps and an endoscope are separately introduced into a body cavity of the patient, and an operator has an image at a tip end portion of the treatment instrument inserted in the body cavity in an observation view field of the endoscope and performs treatment work while observing a treatment state of an affected site by the treatment instrument by the endoscope.

The operator enlarges an image by making the endoscope approach an organ and thereby performs incision or suture of the organ. However, the view field of the operator becomes very narrow. Thus, PTLs 1 to 3 disclose an in-body monitoring camera for widely perceiving a state of the outside of a working area (for example, motion of the treatment instrument on the outside of the working area, a state of bleeding, and a residual state of residues such as gauze).

Further, PTL 4 discloses a capsule endoscope that a patient swallows through a mouth and that thereby captures images of an inside of the body.

CITATION LIST

Patent Literature

PTL 1: Japanese Patent No. 4599474 (issued on Dec. 15, 2010)
PTL 2: International Publication No. WO2015/020124 (published on Feb. 12, 2015)
PTL 3: International Publication No. WO2015/064743 (published on May 7, 2015)
PTL 4: Japanese Patent No. 4422679 (issued on Feb. 24, 2010)

SUMMARY OF INVENTION

Technical Problem

Reliability such as suppression of an adverse influence of internal stray light, air-tightness, and mechanical strength is requested for an in-body image capturing device that captures images while being introduced into a body such as the above-described in-body monitoring camera and capsule endoscope. The present invention suggests an in-body image capturing device that enhances such reliability.

Solution to Problem

An in-body image capturing device according to one aspect of the present invention is an in-body image capturing device including an illumination unit and an image capturing unit that includes a lens, the in-body image capturing device being capable of being introduced into a body, and the illumination unit and the image capturing unit are housed in a casing that is integrally molded with an integral light-transmitting body and an integral light shielding body, the casing includes an illumination cover portion that covers the illumination unit, a lens cover portion that covers the lens, and a lens surrounding portion that surrounds the lens, the illumination cover portion and the lens cover portion are configured with the light-transmitting body, and the lens surrounding portion is configured with the light shielding body, and the lens surrounding portion has an portion that is positioned between the illumination cover portion and the lens cover portion.

Advantageous Effects of Invention

In one aspect of the present invention, an illumination unit and an image capturing unit are housed in a casing that is integrally molded with an integral light-transmitting body and an integral light shielding body. Thus, an adverse influence of internal stray light is suppressed, and air-tightness and mechanical strength are enhanced. Consequently, an in-body image capturing device with high reliability may be realized.

DESCRIPTION OF EMBODIMENTS

Embodiments of the present invention will hereinafter be described based on FIG. 1 to FIG. 25. Note that an outer diameter described below means the maximum outer diameter.

First Embodiment (In-Body Monitoring Camera System)

Figure 1:
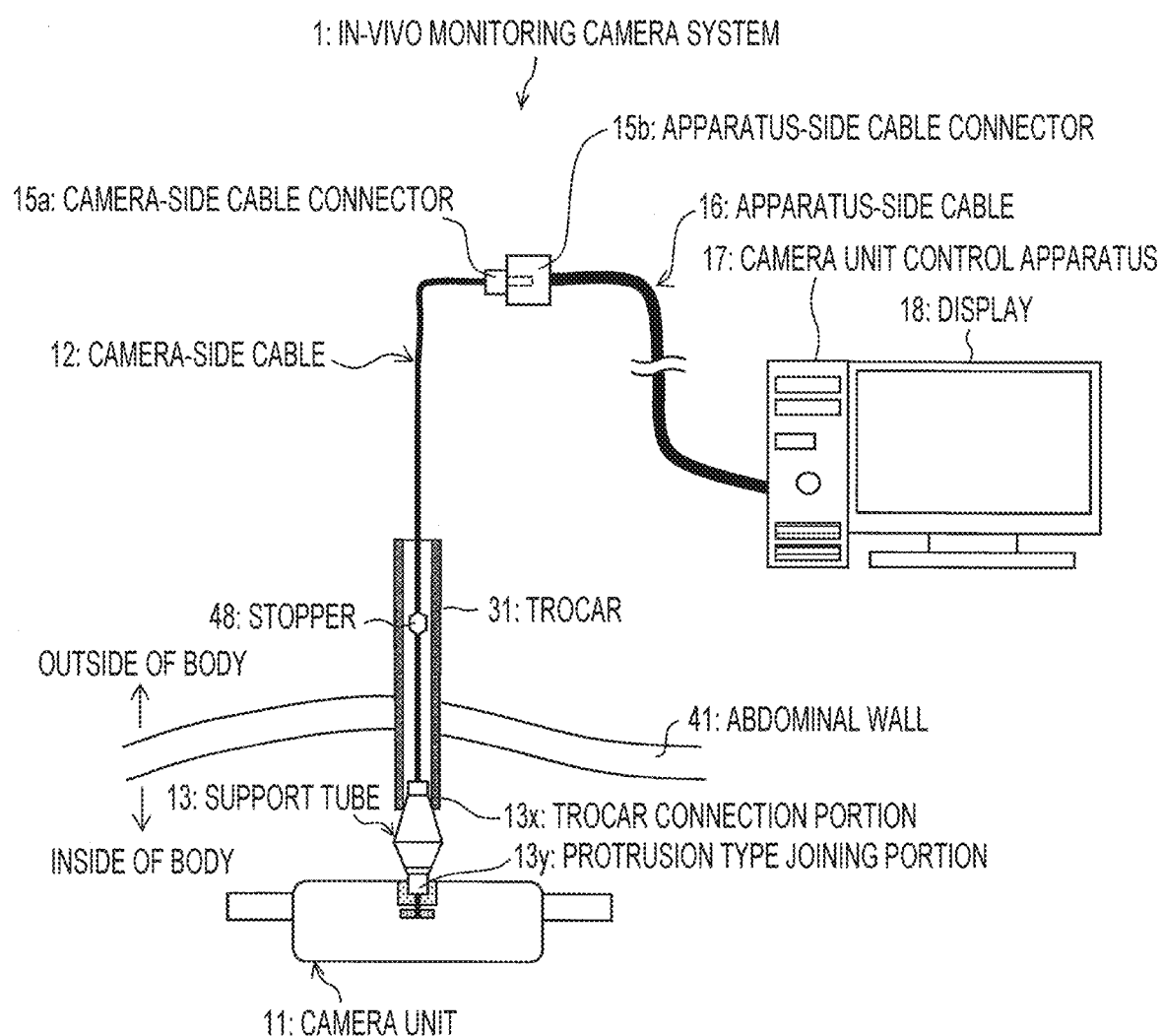
FIG. 1 is a schematic diagram that illustrates a configuration of an in-body monitoring camera system of a first embodiment.

FIG. 1 is a schematic diagram that illustrates a configuration of an in-body monitoring camera system of a first embodiment. As illustrated in FIG. 1, an in-body monitoring camera system 1 includes a camera unit 11 (in-body image capturing device) that has a camera-side cable 12 and is introduced into a body, a support tube (support instrument) 13 that has a trocar connection portion 13x (connection portion) which is used for connection with a trocar 31 (tubular tool) introduced into the body on one end side and has a protrusion type joining portion 13y (joining portion) which is used for joining to the camera unit 11 on the other end side, a control system that includes a camera unit control apparatus 17 and a display 18 (display device), and an apparatus-side cable 16 that connects the camera-side cable 12 and the camera unit control apparatus 17 together.

Note that the camera-side cable 12 has a protrusion type camera-side cable connector 15a on the opposite side to a connection end with the camera unit 11, and the apparatus-side cable 16 has a recess type apparatus-side cable connector 15b on the opposite side to a connection end with the camera unit control apparatus 17. In addition, the camera-side cable 12 has a stopper 48 for restricting movement of the support tube 13 between the connection end with the camera unit 11 and the camera-side cable connector 15a.

Note that a configuration is possible in which a recess type camera-side cable connector and a protrusion type apparatus-side cable connector are fitted together. Further, although one pin of the camera-side cable connector 15a is illustrated in FIG. 1, the number of pins usually corresponds to the number of power lines used for the cable. In the description made below, a camera-side cable connector 15a and an apparatus-side cable connector 15b may be abbreviated as connector 15a and connector 15b, respectively.

In the in-body monitoring camera system 1, an end on the inside of the body of the trocar 31 punctured through an abdominal wall 41 is connected with the support tube 13 by the trocar connection portion 13x, the camera unit 11 introduced into the body is joined to the support tube 13 by the protrusion type joining portion 13y, and the connector 15a of the camera-side cable 12 is drawn out to the outside of the body through the support tube 13 and the trocar 31. Further, the camera-side cable connector 15a is fitted in the apparatus-side cable connector 15b, the camera unit 11 and the camera unit control apparatus 17 are thereby electrically connected together, and a picture photographed by the camera unit 11 is transmitted to the camera unit control apparatus 17. The camera unit control apparatus 17 causes the display 18 to display the picture transmitted from the camera unit 11 and transmits control signals to the camera unit 11. Note that the camera unit control apparatus 17 and the display 18 may be formed integrally or separately.

Here, a wired scheme is employed for transmission from the camera unit 11 to the camera unit control apparatus 17. Thus, the transmission rate may be made high, and high resolution images may be obtained because signals may stably be transmitted and received. Further, communication may be performed with low power compared to a wireless scheme, and size reduction of the camera unit 11 may be intended by supplying a power source from the outside. Accordingly, a wound for introduction of the camera unit 11 into the body may be made small by the size reduction, thus providing an effect of improving minimal invasiveness.

(Camera Unit)

Figure 2:
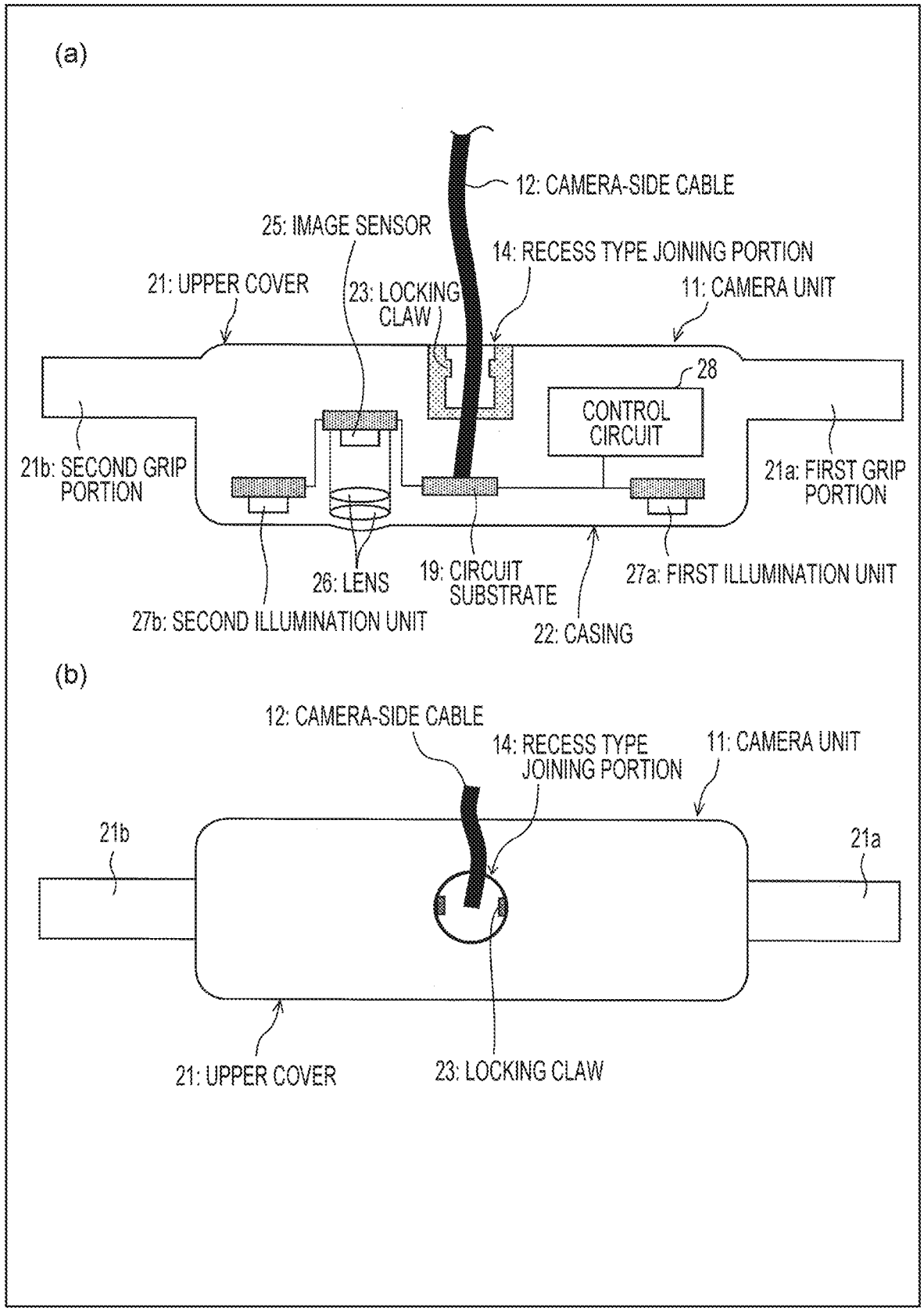
FIG. 2 is a cross-sectional diagram (a) and a top diagram (b) that illustrate a configuration of a camera unit of the first embodiment.

FIG. 2 is a cross-sectional diagram (a) and a top diagram (b) that illustrate a configuration of a camera unit of the first embodiment. As illustrated in (a) and (b) in FIG. 2, the camera unit 11 has a circuit substrate 19, an image capturing unit that includes an image sensor 25 and lenses 26, a control circuit 28, and first and second illumination units 27a and 27b in an internal portion of a camera housing (described later in detail) that is formed with an upper cover 21 and a casing 22. The camera-side cable 12, the image capturing unit, the control circuit 28, and the illumination units 27 are connected with the circuit substrate 19. The control circuit 28 may be built in the circuit substrate 19.

A recess type joining portion 14 is provided on an upper surface of the upper cover 21. The recess type joining portion 14 has a hole structure with a circular opening and is provided with a locking claw 23 on an inner wall. Both end portions of the upper cover 21 are first and second grip portions 21a and 21b. The first and second grip portions 21a and 21b are grasped when the camera unit 11 is introduced into the body by using forceps or grasped such that the upper cover 21 faces the protrusion type joining portion 13y of the support tube 13 when the camera unit 11 and the support tube 13 are joined together.

The camera-side cable 12 connected with the circuit substrate 19 is guided to the outside of the camera unit 11 so as to pass through an internal portion of the recess type joining portion 14. A connection part between the circuit substrate 19 and the camera-side cable 12 is sealed by a resin or the like. In addition, in a portion (a bottom portion of the recess type joining portion 14) from which the camera-side cable 12 is drawn out in the internal portion of the recess type joining portion 14, the camera-side cable 12 is bonded and fixed to the bottom portion of the recess type joining portion 14. For example, sealed fixing by an adhesive or an O-ring is performed. A configuration is thereby made which avoids occurrence of flooding, entrance of a foreign object, or the like (into the camera unit 11) from this portion. The camera-side cable 12 is introduced into the body cavity through a trocar and is thus formed of a flexible material.

The image sensor 25 is a CCD, a CMOS image sensor, or the like, and the first and second illumination units 27a and 27b illuminate the inside of the body and thereby make pictures photographed by the camera unit 11 clear. The first and second illumination units 27a and 27b are preferably of a small size, and an LED or the like is suitably used, for example.

Further, a film on a surface of the camera-side cable 12 (including the connector 15a) is desirably formed to be blue or green. In such a manner, blue and green in the complementary color relationship with colors of the inside of the body such as red and yellow, specifically, colors that correspond to visible light at wavelengths of 420 to 570 nm (particularly preferably 450 to 530 nm) are used, and installation work and collection work in the body, which will be described later, may thereby be facilitated.

Figure 3:
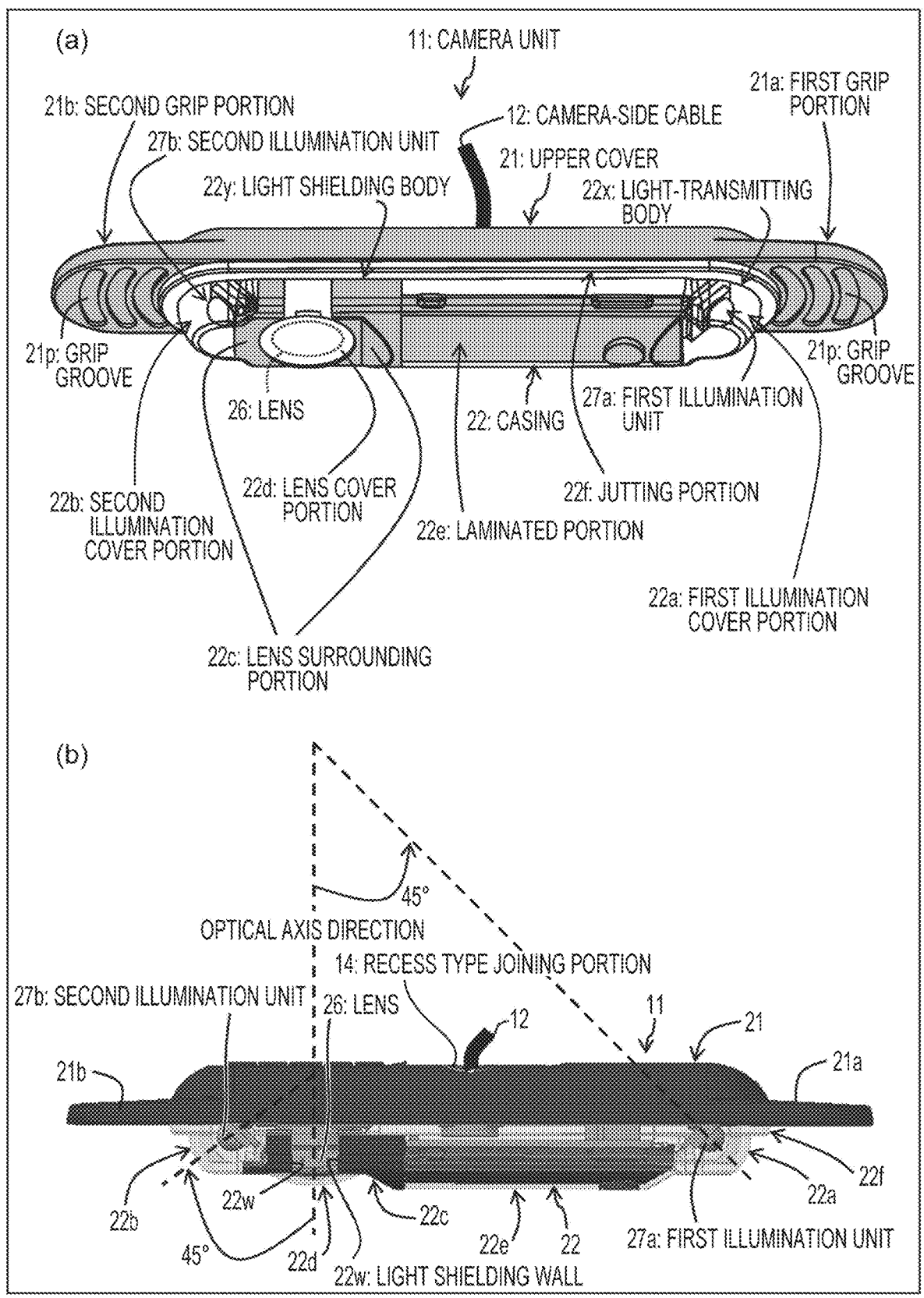
FIG. 3 is a perspective diagram (a) as seen from a bottom side and a front diagram (b) that illustrate the configuration of the camera unit of the first embodiment.
Figure 4:
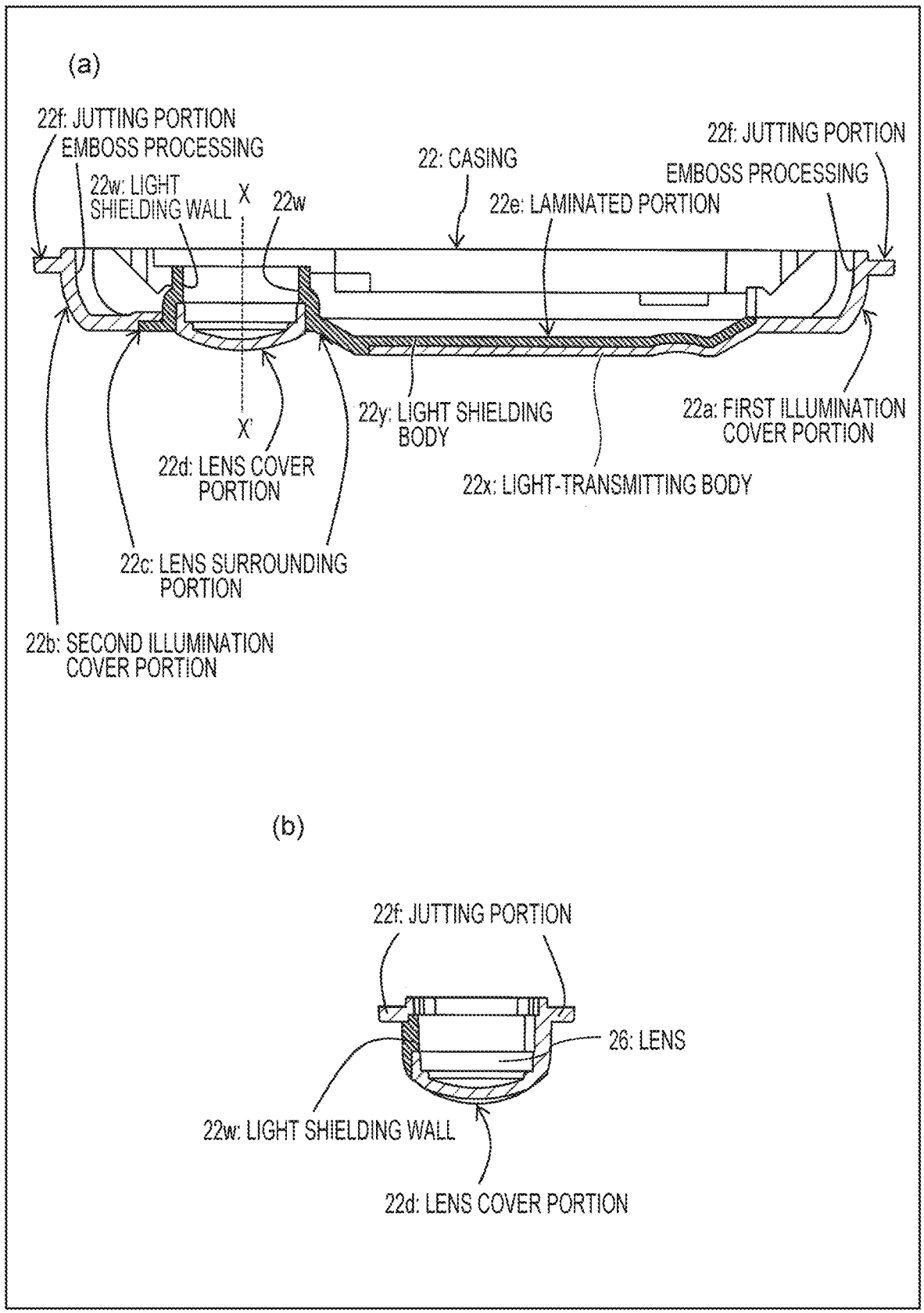
FIG. 4 is a longitudinal cross-sectional diagram (a) in the longitudinal direction and a longitudinal cross-sectional diagram (b) in a perpendicular direction to the longitudinal direction that illustrate the configuration of the camera unit of the first embodiment.

FIG. 3 is a perspective diagram (a) as seen from a bottom side and a front diagram (b) that illustrate the configuration of the camera unit of the first embodiment. FIG. 4 is a longitudinal cross-sectional diagram (a) in the longitudinal direction and a longitudinal cross-sectional diagram (b) in a perpendicular direction to the longitudinal direction (a portion passing through line X-X' in (a)) that illustrate the configuration of the camera unit of the first embodiment.

As illustrated in FIG. 3 and FIG. 4, the camera unit 11 is formed into a ship shape that is easily placed through the tubular tool, and the image capturing unit (the lens 26 and an image sensor that is not illustrated), a circuit substrate and a control circuit that are not illustrated, and the first and second illumination units 27a and 27b are housed between the upper cover 21 and the casing 22.

The casing 22 has a thin-long shape, the first and second illumination units 27a and 27b are arranged in two end portions (tip end portions) in the longitudinal direction, and the lens 26 is provided between the first and second illumination units 27a and 27b.

The upper cover 21 has a thin-long shape, two end portions (tip end portions) in the longitudinal direction form the first and second grip portions 21a and 21b, and the recess type joining portion 14 is formed in a central portion. The first and second grip portions 21a and 21b are in a flat-plate shape, and plural finger-print-like grip grooves (recesses) 21p for preventing slip are formed in each of upper surfaces and lower surfaces. Further, the upper cover 21 curves so as to be protruded upward (toward the opposite side to the casing 22).

The casing 22 is integrally molded with an integral light-transmitting body (for example, a transparent body) 22x and an integral light shielding body 22y (an object with lower light transmittance than the light-transmitting body 22x) and includes a first illumination cover portion 22a that covers the first illumination unit 27a, a second illumination cover portion 22b that covers the second illumination unit 27b, a lens surrounding portion 22c that surrounds the lens 26, a lens cover portion 22d that covers the lens 26, and a jutting portion 22f that juts outward from the vicinity of an opening of the casing 22. The first and second illumination cover portions 22a and 22b, the lens cover portion 22d, and the jutting portion 22f are configured with the light-transmitting body, and the lens surrounding portion 22c is configured with the light shielding body. The casing 22 further includes a laminated portion 22e whose outside is configured with the light-transmitting body 22x and whose inside is configured with the light shielding body 22y between the first illumination cover portion 22a and the lens surrounding portion 22c.

The lens surrounding portion 22c has a light shielding wall 22w that is positioned between the lens 26 and the first and second illumination units 27a and 27b. Further, the lens cover portion 22d is in an outward protruded shape. Further, processing for providing protrusions and recesses on a surface, which is referred to as emboss processing, specifically, a beading (blasting) process or the like is applied to internal surfaces of the first and second illumination cover portions 22a and 22b.

The jutting portion 22f of the casing 22 is a margin for welding, and a jutting portion 22f of the casing 22 and the upper cover 21 are laser-welded together.

Further, the first and second illumination units 27a and 27b are disposed such that the light irradiation directions thereof (directions in which the light amount becomes the maximum) are inclined at 45° in directions to separate from the lens 26 with respect to the optical axis direction of the lens 26. This inclination angle is decided in accordance with the image capturing angle (viewing angle). For example, in a case where the viewing angle of the camera unit 11 is 130°, an inclination of 45° is desirable for optimizing the light distribution. Further, in a case where the minimum viewing angle for which no more consideration may be requested is set as 85°, an inclination of 30° is desirable for optimizing the light distribution.

Further, the camera-side cable 12 that is connected with the circuit substrate in the casing 22 is drawn out to the outside through the internal portion of the recess type joining portion 14 that is provided in the central portion of the upper cover 21.

Figure 5:
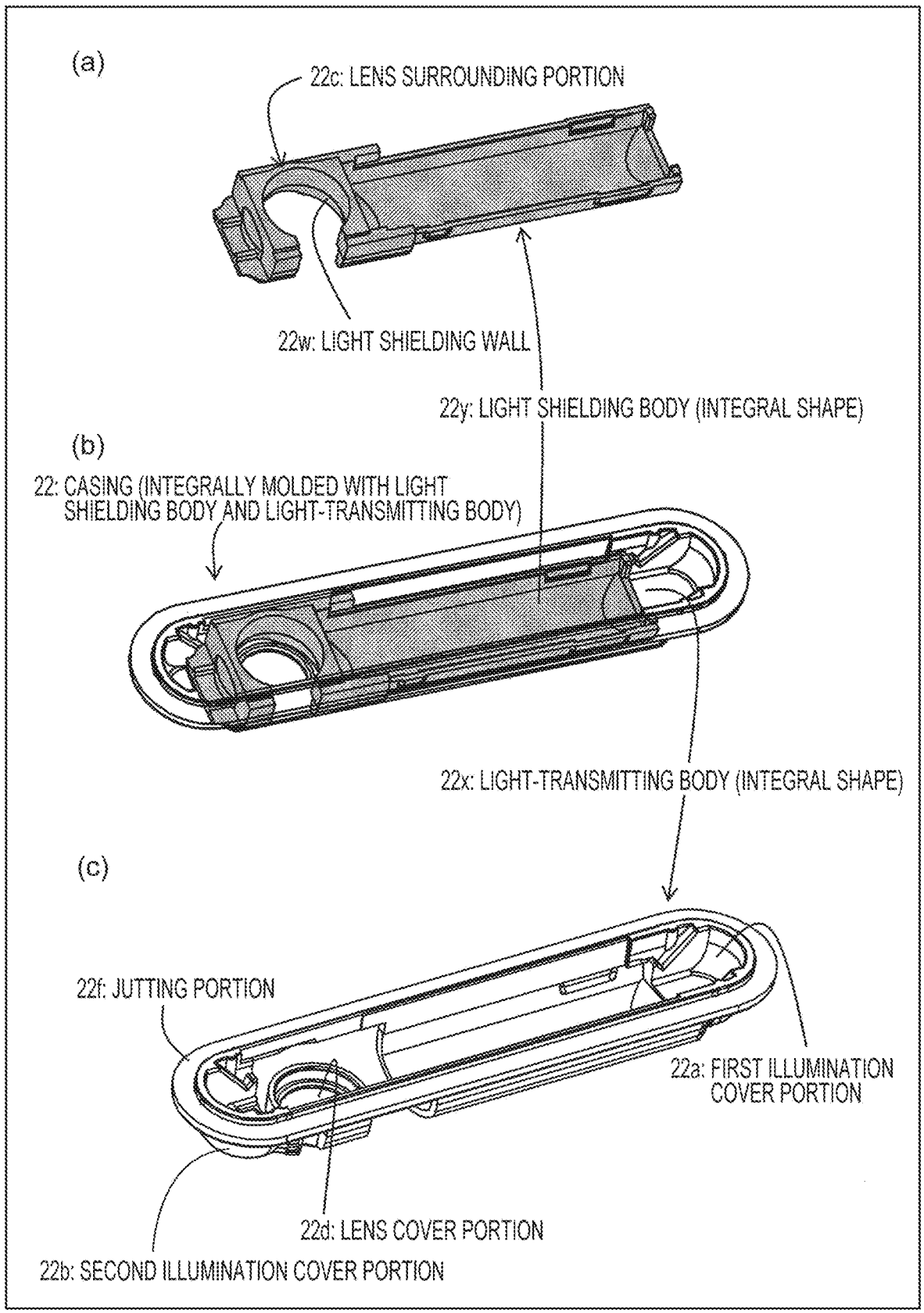
FIG. 5 is a perspective diagram (a) that illustrates a light shielding body of a casing of the camera unit, a perspective diagram (b) that illustrates the whole casing, and a perspective diagram (c) that illustrates a light-transmitting body of the casing.

The casing 22 illustrated in FIG. 3 and FIG. 4 is obtained, for example, by fitting the light shielding body 22y that is in advance molded in an interior of a die of the whole casing, pouring a transparent resin into gaps in the die, and thereby integrally molding (insert molding) the light-transmitting body 22x and the light shielding body 22y (see (b) in FIG. 5). Note that a black resin is poured into an interior of a die of the light shielding body 22y and hardened in the same molding machine, the hardened black resin is next placed in the die of the whole casing, the transparent resin is poured therein, and the light-transmitting body 22x and the light shielding body 22y may thereby be integrally molded (two-color molding). By any of the schemes, as illustrated in (a) in FIG. 5, the light shielding body 22y that includes the lens surrounding portion 22c is formed as an integral shape. As illustrated in (c) in FIG. 5, the light-transmitting body 22x that includes the first and second illumination cover portions 22a and 22b, the lens cover portion 22d, and the jutting portion 22f is formed as an integral shape.

Figure 6:
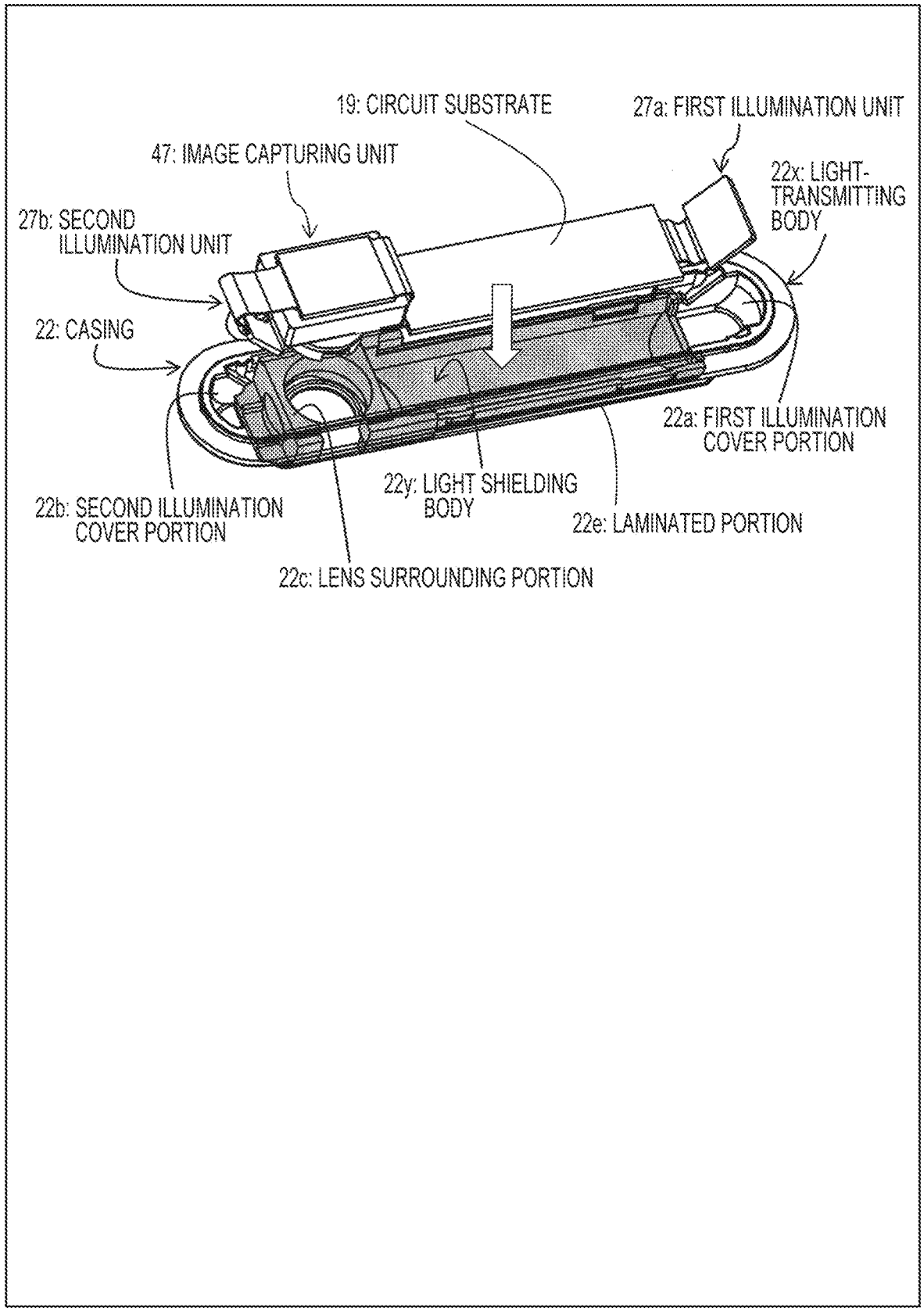
FIG. 6 is a perspective diagram that illustrates manufacturing steps of the camera unit (housing of a circuit substrate and illumination units in the casing).
Figure 7:
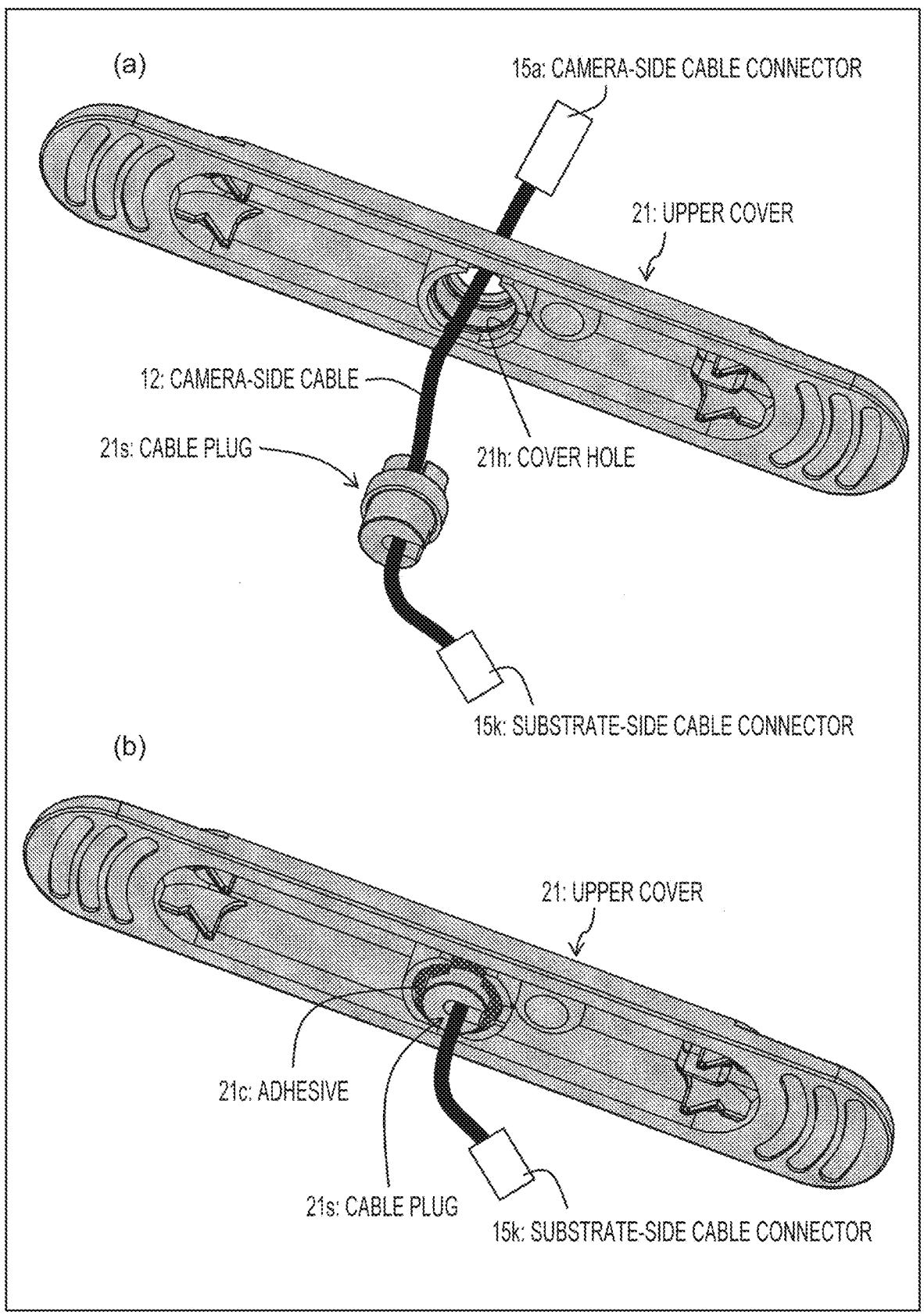
FIG. 7 is perspective diagrams (a) and (b) that illustrate the manufacturing steps of the camera unit (drawing out and fixing of a cable).
Figure 8:
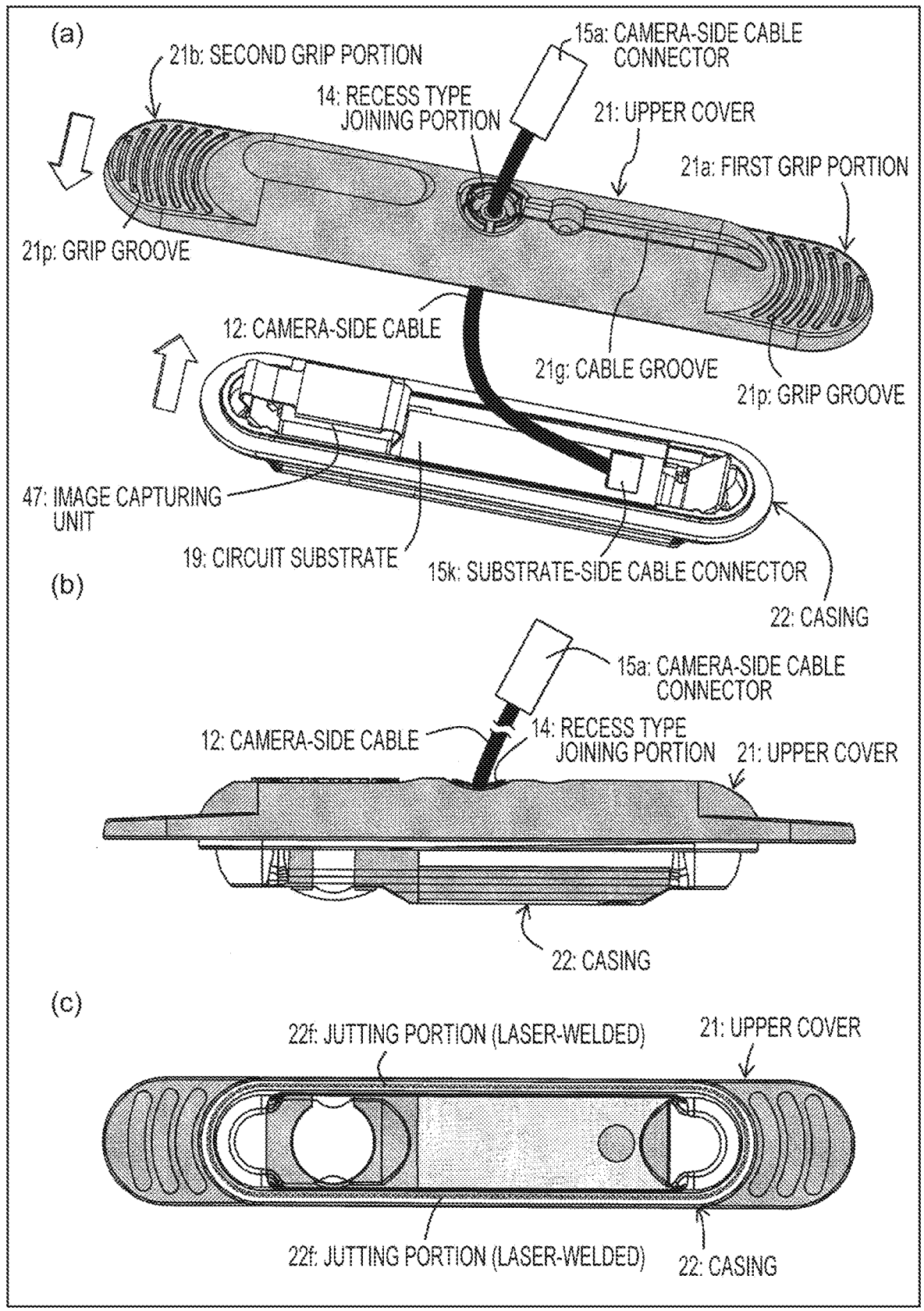
FIG. 8 is perspective diagrams (a) to (c) that illustrate the manufacturing steps of the camera unit (welding of the casing and an upper cover).
Figure 9:
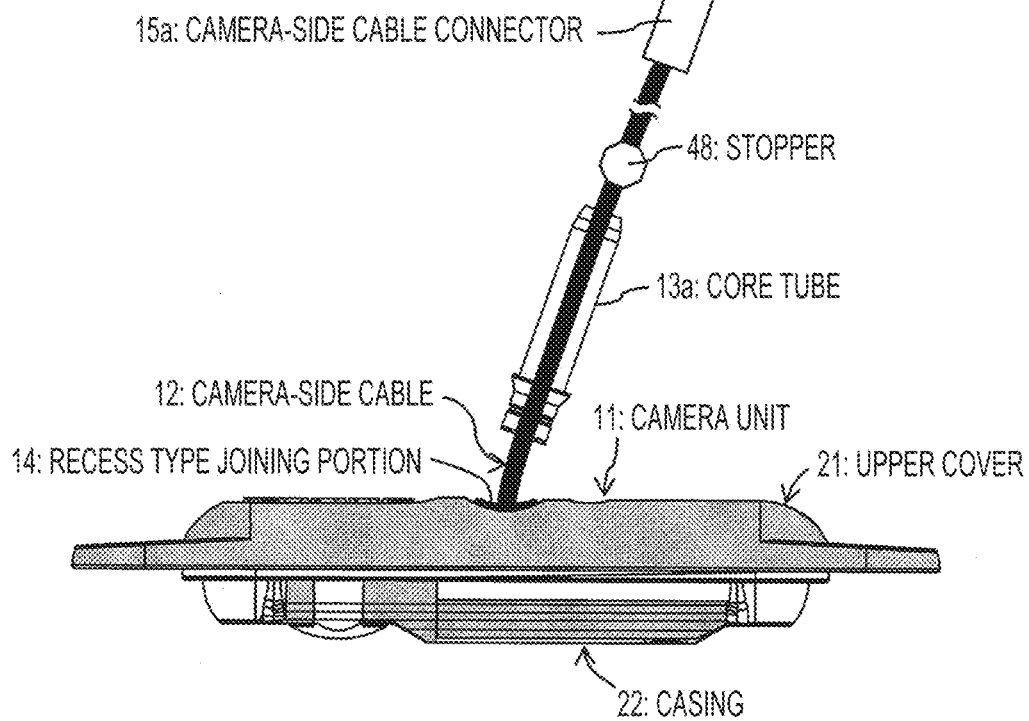
FIG. 9 is perspective diagrams (a) and (b) that illustrate the manufacturing steps of the camera unit (installation of a support tube).
Figure 9:
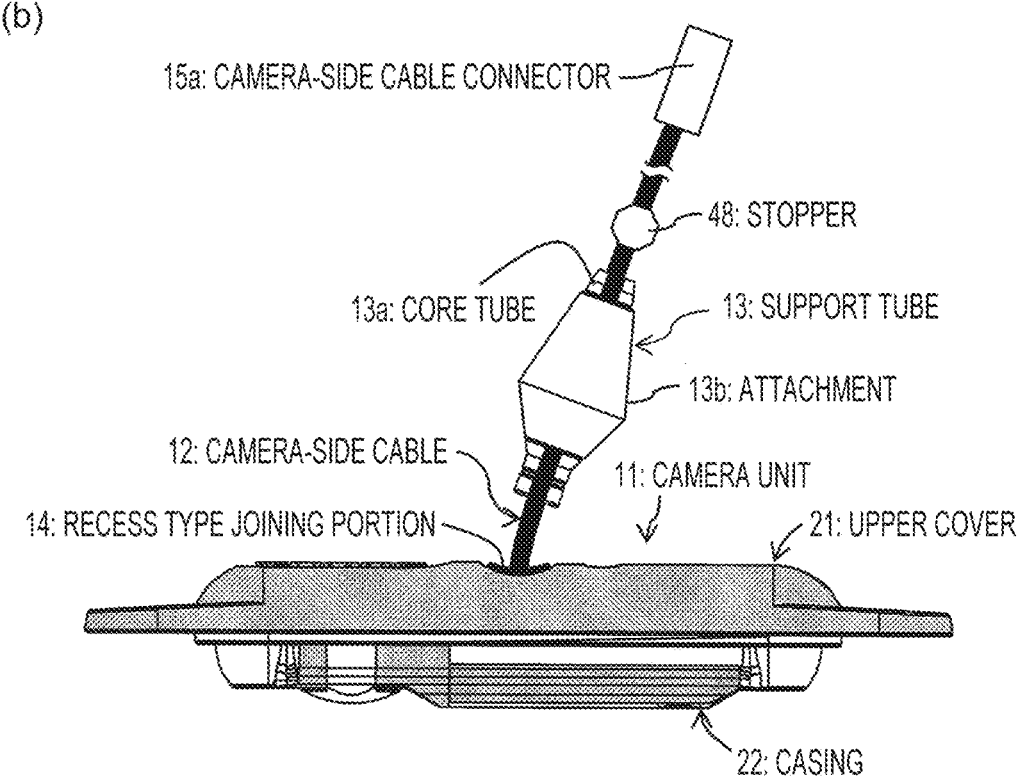
Figure 10:
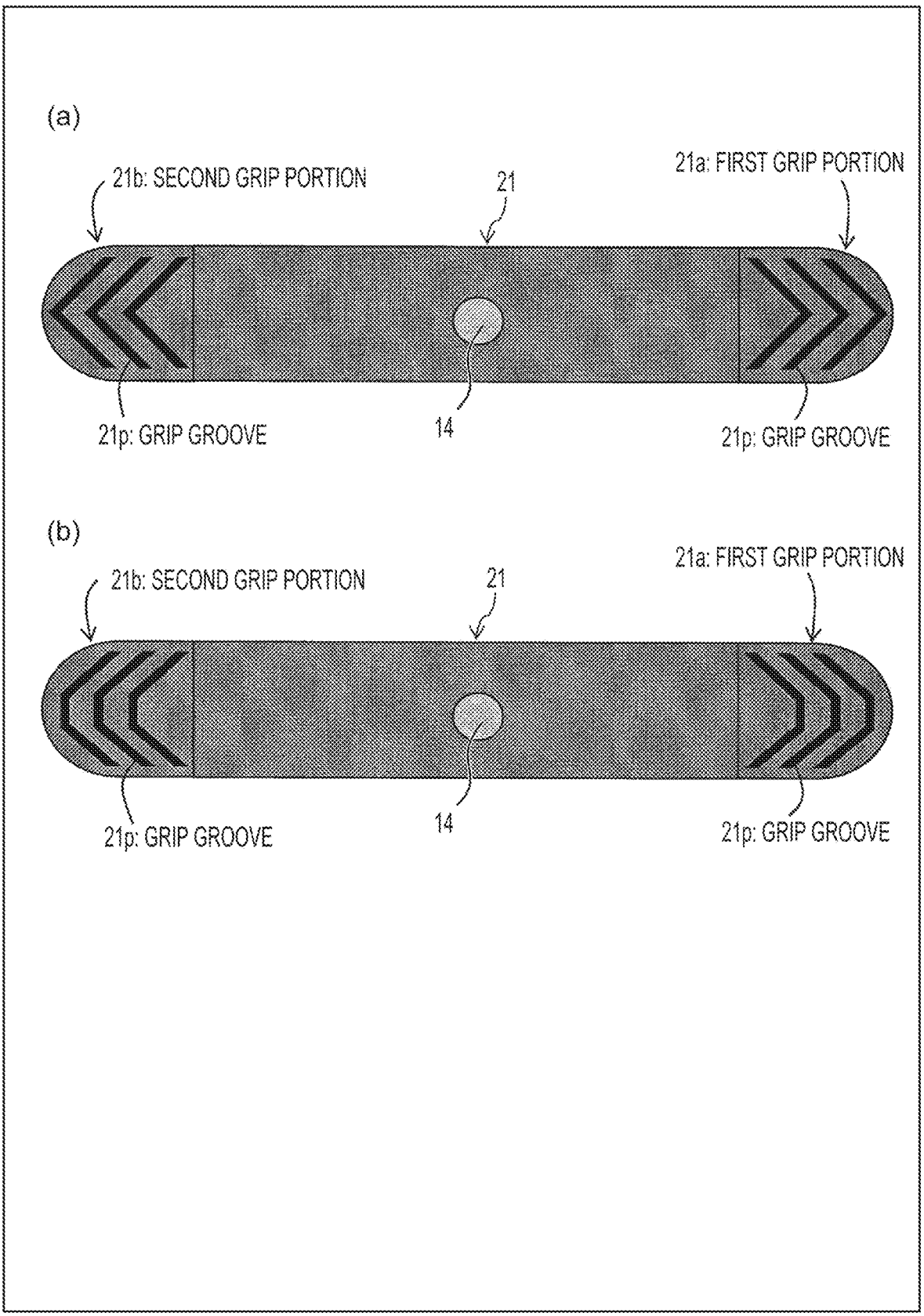
FIG. 10 is plan diagrams (a) and (b) that illustrate grip grooves formed in grip portions of the upper cover.

FIG. 6 is a perspective diagram that illustrates housing of the circuit substrate and the illumination units in the casing among manufacturing steps of the camera unit. FIG. 7 is perspective diagrams (a) and (b) that illustrate drawing out and fixing of the cable among the manufacturing steps of the camera unit. FIG. 8 is perspective diagrams (a) to (c) that illustrate welding of the casing and the upper cover among the manufacturing steps of the camera unit. FIG. 9 is perspective diagrams (a) and (b) that illustrate installation of the support tube among the manufacturing steps of the camera unit.

After the casing 22 is molded as described earlier, as illustrated in FIG. 6, an image capturing unit 47 (including the lens and the image sensor), the circuit substrate 19 (in which the control circuit is built), and the first and second illumination units 27*a* and 27*b* are housed in an internal portion of the casing 22. Here, the lens is accommodated in the lens surrounding portion 22*c*, the first illumination unit 27*a* is accommodated in the first illumination cover portion 22*a*, the second illumination unit 27*b* is accommodated in the second illumination cover portion 22*b*, and the circuit substrate 19 is accommodated on the laminated portion 22*e*.

Next, as illustrated in (a) and (b) in FIG. 7, the camera-side cable connector 15*a* is placed through a cover hole 21*h* that penetrates the central portion of the upper cover 21 from the back side of the upper cover 21. Note that the camera-side cable 12 has the camera-side cable connector 15*a* at one end and has a substrate-side cable connector 15*k* at the other end, and a cable plug 21*s* is placed around between the camera-side cable connector 15*a* and the substrate-side cable connector 15*k*. Next, the cable plug 21*s* through which the camera-side cable 12 places is fitted in a lower portion of the cover hole 21*h*, the cable plug 21*s* and the upper cover 21 are adhered and fixed together by an adhesive 21*c* arranged around the cable plug 21*s*. Note that an upper portion of the cover hole 21*h* is the recess type joining portion 14, and the camera-side cable 12 is drawn out to the outside through the internal portion of the recess type joining portion 14.

Next, as illustrated in (a) to (c) in FIG. 8, the upper cover 21 is arranged on the opening of the casing 22, the jutting portion 22*f* of the casing 22 is irradiated with laser from a bottom surface (lower surface) of the casing 22, and the jutting potion 22*f* and the upper cover 21 are thereby laser-welded together. Note that as illustrated in (a) in FIG. 8, a cable groove 21*g* that adjoins the recess type joining portion 14 is formed in the upper surface of the upper cover 21. The cable groove 21*g* is for accommodating a portion of the camera-side cable 12 when the camera unit 11 is placed through the tubular tool (a trocar or the like).

Next, as illustrated in (a) and (b) in FIG. 9, the camera-side cable 12 passes through the stopper 48 and a core tube 13*a*, which is an inner member of the support tube 13, and an attachment 13*b*, which is an outer member of the support tube 13, is further fitted on the core tube 13*a* through the camera-side cable 12 from the camera-side cable connector 15*a* side.

In the camera unit 11, the image capturing unit, the circuit substrate 19, and the first and second illumination units 27*a* and 27*b* are housed in the casing 22 that is integrally molded with the integral light-transmitting body 22*x* and the integral light shielding body 22*y*. Thus, an adverse influence of stray light in the casing is suppressed, and air-tightness and mechanical strength are enhanced as well. Consequently, an in-body image capturing device with high reliability may be realized.

Further, because the casing 22 is provided with the first and second illumination cover portions 22*a* and 22*b*, the lens cover portion 22*d*, and the lens surrounding portion 22*c*, the stray light in the casing is suppressed, and the lens 26 and the first and second illumination units 27*a* and 27*b* are not exposed to the outside. Thus, reliability may be enhanced.

In the casing 22, because the lens surrounding portion 22*c* has the light shielding wall 22*w*, the adverse influence on image capturing by the stray light in the internal portion of the casing may be reduced more effectively.

Because the casing 22 includes the laminated portion 22*e* whose outside is configured with the light-transmitting body 22*x* and whose inside is configured with the light shielding body 22*y*, the mechanical strength of the casing may be enhanced.

In the casing 22, the jutting portion 22*f* that juts outward from the vicinity of the opening may be used as a margin for laser welding, and the air-tightness and mechanical strength of the casing may thereby be enhanced.

In the camera unit 11, the irradiation directions of the first and second illumination units 27*a* and 27*b* are inclined in the directions to separate from the lens with respect to the optical axis direction of the lens. Thus, the adverse influence on the image capturing by the stray light in the internal portion of the casing may effectively be reduced.

In the casing 22, because the emboss processing (for example, a sandblasting process, a beading process, or the like) is applied to the internal surfaces of the first and second illumination cover portions 22*a* and 22*b*, light scattering by the first and second illumination cover portions 22*a* and 22*b* increases, and the adverse influence on the image capturing by the stray light in the internal portion of the casing may thereby be reduced effectively. Further, because the illumination light to the inside of the body may effectually be diffused, a wide image capturing angle may be realized.

In the casing 22, because the upper cover 21 and the jutting portion 22*f* are laser-welded together, the air-tightness and mechanical strength of the casing may be enhanced.

In the camera unit 11, because the plural finger-print-like grip grooves 21*p* are formed in each of the upper surfaces and lower surfaces of the first and second grip portions 21*a* and 21*b*, the grip grooves 21*p* provide an effect of preventing slip, and it becomes easy to grip the camera unit 11.

Note that both of the end portions (tip end portions) of the upper cover 21 in an elongated shape are formed as the first and second grip portions 21*a* and 21*b*. However, the shape of the grip groove 21*p* that is formed in at least one of the upper surfaces and the lower surfaces of the first and second grip portions 21*a* and 21*b* is not limited to a curve shape (arc shape) as illustrated in FIG. 3 and FIG. 8 but may be a straight line shape or a polygonal line shape. For example, as illustrated in (a) and (b) in FIG. 10, the grip groove 21*p* may be formed into a hook shape (polygonal line shape) that extends from a position in proximity to one edge along the longitudinal direction of the upper cover 21 toward a position in proximity to the other edge along the longitudinal direction.

In the casing 22, because a cable joining portion (cable plug 21*s*) and the first and second grip portions 21*a* and 21*b* on which mechanical loads are exerted in installation or collection of the camera unit are provided to the same upper cover 21, the mechanical strength is enhanced. Note that considering a case where the cable joining portion (cable plug) is provided to the upper cover and the first and second grip portions are provided to the casing, external forces in the opposite directions (external forces to tear the welded portion between the casing and the upper cover) is possibly added to both of the cable joining portion and the first and second grip portions. However, such a possibility is avoided in a case where both of those are provided to the upper cover 21.

In the casing 22, the lens cover portion 22d is in an outward protruded shape. Thus, a wide image capturing angle may be realized. Further, even in a case where dirt sticks on the lens cover portion 22d in surgery, it is easy for an operator to wipe the dirt by gauze or the like pinched between forceps.

(Configuration and Function of Support Tube)

Figure 11:
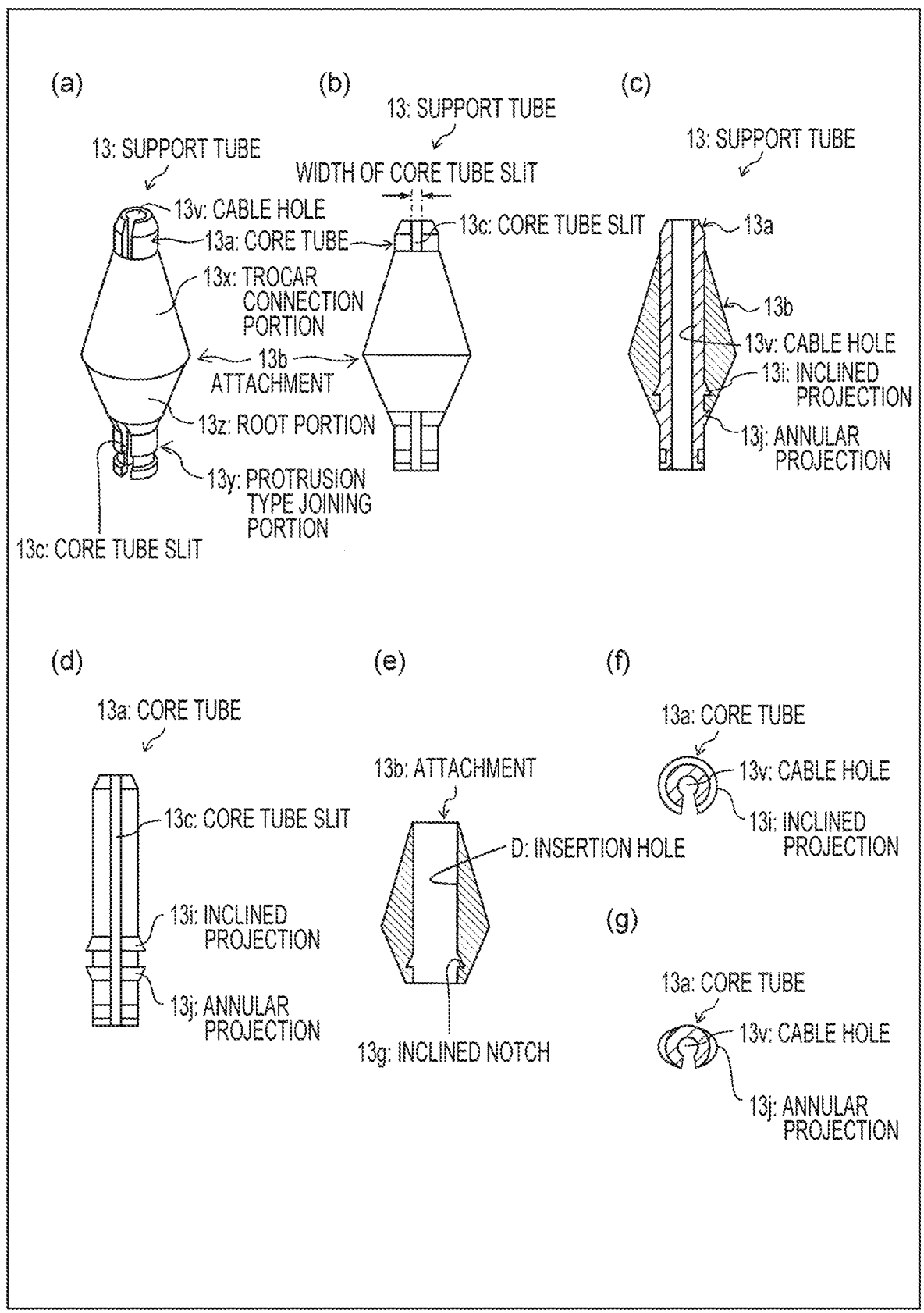
FIG. 11 is a perspective diagram (a), front diagrams (b) and (d), and cross-sectional diagrams (c), (e), (f), and (g) that illustrate a configuration of the support tube in the first embodiment.

FIG. 11 is a perspective diagram (a), front diagrams (b) and (d), and cross-sectional diagrams (c), (e), (f), and (g) that illustrate a configuration of the support tube.

The support tube 13 has the trocar connection portion 13x used for connection with the trocar on one end side and has the protrusion type joining portion 13y on the other end side. The recess type joining portion 14 of the camera unit 11 is fitted in the protrusion type joining portion 13y of the support tube 13, and the support tube 13 and the camera unit 11 are thereby joined together. The protrusion type joining portion 13y is pulled out from the recess type joining portion 14 of the camera unit 11, and the support tube 13 is thereby separated from the camera unit 11.

As illustrated in FIG. 11, the support tube 13 is configured with the core tube 13a that has a cable hole 13v (circular opening) and the attachment 13b that is attached to the outside surface of the core tube 13a. A core tube slit 13c that longitudinally crosses the core tube 13a from one opening to the other opening of the core tube 13a is formed in the core tube 13a. The hole diameter (the inner diameter of the support tube 13) of the cable hole 13v is smaller than the outer diameter of the camera-side cable connector.

As illustrated in (a) and (b) in FIG. 11, the attachment 13b is in a spindle shape that has the insertion hole D (circular opening) and is formed with the trocar connection portion 13x in a truncated conical shape that becomes thinner in the direction to approach the trocar 31 and a root portion 13z in a truncated conical shape that becomes thinner in the direction to approach the camera unit 11. Further, the support tube 13 is configured by fitting the core tube 13a in the insertion hole D of the attachment 13b and thereby mounting the attachment 13b on the core tube 13a. Here, the attachment 13b is configured such that the camera-side cable connector 15a may be placed through the inside of the insertion hole D.

Note that in the core tube 13a, the lower portion (an end portion on the camera unit 11 side) on which the attachment 13b is not mounted serves as the protrusion type joining portion 13y.

As illustrated in (c) to (g) in FIG. 11, two inclined projection 13i that are opposed to each other are formed on the outside surface of the core tube 13a, and an annular projection 13j around the whole outer circumference is formed on a lower side (camera unit side) of the inclined projections 13i. Further, two inclined notches 13g that are opposed to each other are formed in the vicinity of the lower edge of the attachment 13b. Further, the attachment 13b is fitted on the outside of the core tube 13a from up to down, the inclined notches 13g are thereby locked in the inclined projections 13i, and the lower edge of the attachment 13b is supported by the annular projection 13j. Note that fixing by an adhesive may be performed in this state. Note that the inclined projection 13i on the upper side is made smaller than the annular projection 13j on the lower side, the two inclined projections 13i on the upper side are provided as illustrated in (g) in FIG. 11, and the attachment 13b thereby warps and facilitates fitting. Further, the annular projection 13j is provided on the lower side, and the durability against the downward stress may thereby be enhanced.

The core tube slit 13c is used in a case where the camera-side cable is placed through the core tube 13a from a side surface. Thus, as illustrated in (f) and (g) in FIG. 11, it is desirable that the slit width is configured to become smaller from an outside surface toward an inside surface and that it is difficult for the camera-side cable that is once placed through the core tube slit 13c to be removed.

Note that an inside surface (wall surfaces of the cable holes) of the support tube 13 desirably contacts with the camera-side cable 12 such that the support tube 13 is moderately retained in an intermediate position of the camera-side cable 12 (the vicinity of the camera unit 11) (in a state where the support tube 13 is retained in the position by the cable unless a force is particularly added but is movable along the cable in a case where a light force is added). If the support tube 13 is in a state where no contact resistance is present, in a case where installation work is performed by pinching the camera unit 11 by forceps, the support tube 13 moves (dangles) toward the connector 15a side at each time when the camera unit 11 is moved, the position of a cable end (connector 15a) is thus not fixed, and the efficiency of the installation work lowers.

(Using Method of In-Body Monitoring Camera System)

Figure 12:
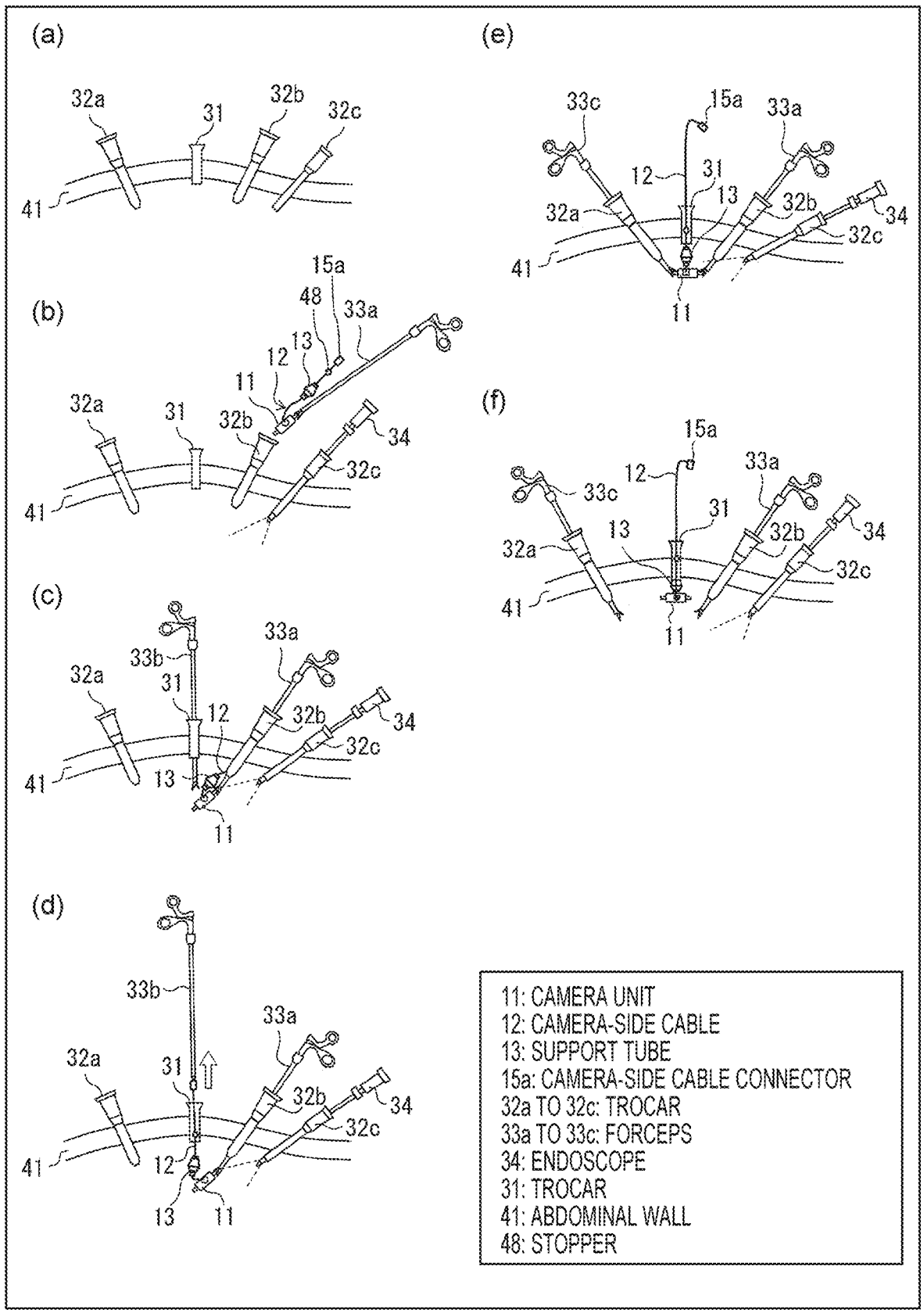
FIG. 12 is schematic diagrams (a) to (f) that illustrate use examples of the support tube, the camera unit, and trocars in the first embodiment.
Figure 13:
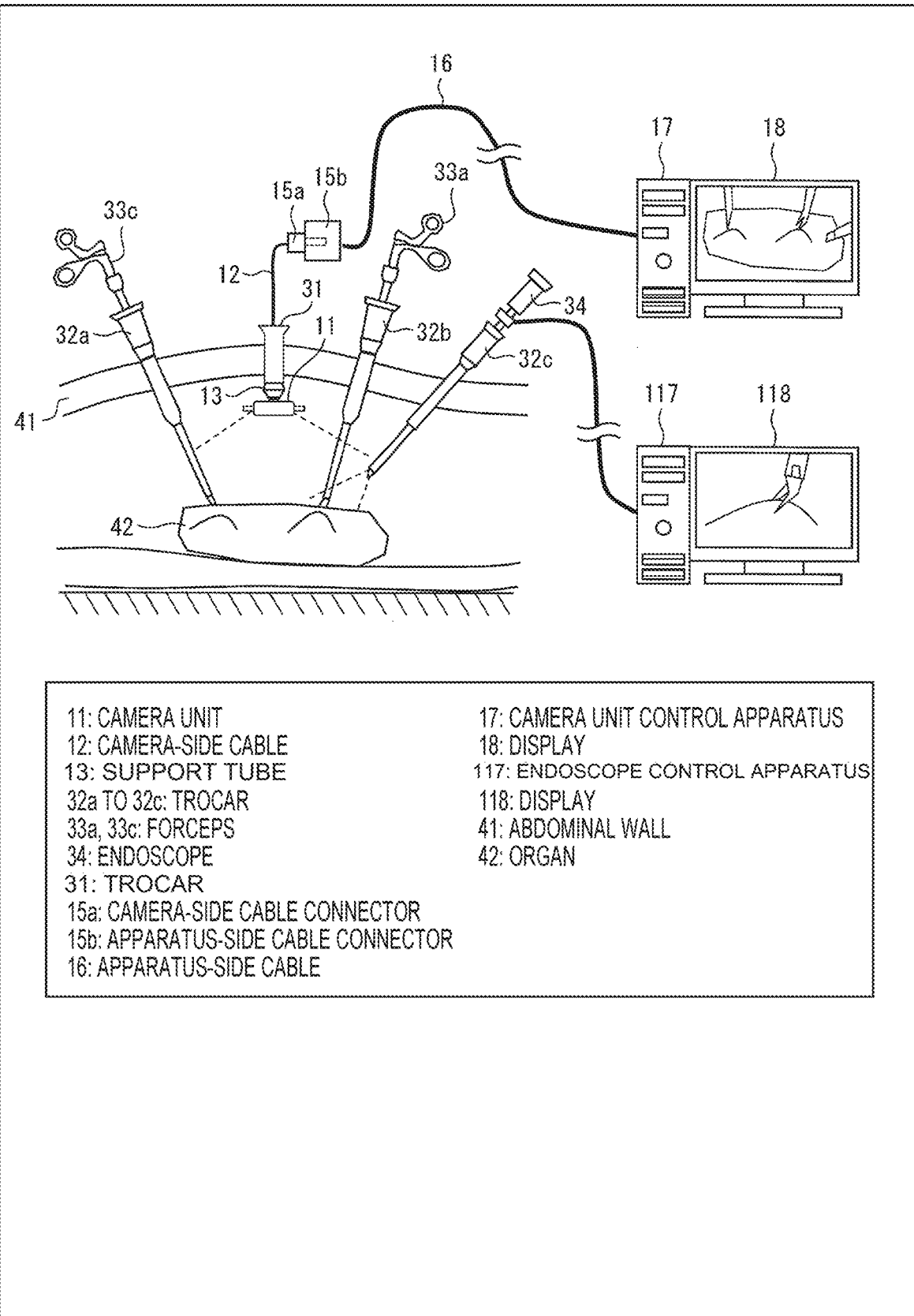
FIG. 13 is a schematic diagram that illustrates a use example of the in-body monitoring camera system of the first embodiment.

(a) to (f) in FIG. 12 are schematic diagrams that illustrate an installation method of the camera unit in the body in the first embodiment. FIG. 13 is a schematic diagram that illustrates a use situation of the in-body monitoring camera system of the first embodiment.

As illustrated in (a) in FIG. 12, the operator first opens holes (ports) for inserting forceps and an endoscope in the body cavity in the abdominal wall 41 and inserts trocars 32a to 32c in the ports. In addition, in order to install the camera unit 11 in the body cavity, the port is opened in a position in the abdominal wall 41 from which the whole organ including an affected site may be seen, and the trocar 31 is inserted therein. Specifically, in a state where a needle-shaped obturator is placed through the inside of the trocar 31, the obturator is punctured into a port position, and the trocar 31 is thereby inserted in the abdominal wall 41. Further, the trocar 31 preferably has a short diameter in order to realize minimal invasiveness. Specifically, the trocar 31 preferably has a diameter of 3 mm or less. Note that after at least one of the trocars 32a to 32c and the trocar 31 is inserted, the operator sends gas into the body through the trocar, in advance inflates the body cavity, and thereby secures a space to insert tools.

Next, as illustrated in (b) in FIG. 12, the operator inserts an endoscope 34 in the body cavity through the trocar 32c and inserts the camera unit 11 grasped by forceps 33a, the camera-side cable 12, and the support tube 13 through which the camera-side cable 12 places in the body cavity through the trocar 32b while observing the inside of the body by using the endoscope 34.

Next, as illustrated in (c) in FIG. 12, the operator moves the camera unit 11 to the vicinity of the trocar 31 by operating the forceps 33a and inserts forceps 33b in the body cavity through the trocar 31.

Next, as illustrated in (d) in FIG. 12, the operator pulls out the forceps 33b from the trocar 31 in a state where the camera-side cable 12 is pinched by the forceps 33b and thereby guides the camera-side cable 12 to the outside of the body. Here, the camera unit 11 (the grip portion thereof) is grasped by the forceps 33a.

Next, as illustrated in (e) in FIG. 12, the operator draws up the camera-side cable 12 guided to the outside of the body by forceps, a hand, or the like and thereby brings a tip end of the support tube 13 to proximity of the opening of the trocar 31.

Next, as illustrated in (f) in FIG. 12, the operator further draws up the camera-side cable 12 and the camera unit 11, thereby inserts one end (trocar connection portion) of the support tube 13 into the end portion of the trocar 31 on the inside of the body, fits the camera unit 11 in the other end (protrusion type joining portion), thereby connects the one end (trocar connection portion) of the support tube 13 with the end portion of the trocar 31 on the inside of the body, joins the other end (protrusion type joining portion) to the camera unit 11, and thereby fixes the camera-side cable 12 to the abdominal wall 41 or the like such that the tension of the camera-side cable 12 is maintained.

After the camera unit 11 is installed in the body, as illustrated in FIG. 13, the connector 15a of the camera-side cable 12 is fitted in the apparatus-side cable connector 15b, and the camera-side cable 12 is thereby connected with the apparatus-side cable 16. Consequently, local pictures of a treatment site are displayed on a display 118 by an endoscope control apparatus 117, and a whole picture of the inside of an organ 42, which is photographed by the camera unit 11, is displayed on the display 18 by the camera unit control apparatus 17.

The following is performed after the use. First, the operator puts forceps 33c into the gap between the support tube 13 and the camera unit 11 in a state where the first or second grip portion 21a or 21b of the camera unit 11 in the body is grasped by the forceps 33a and operates the forceps 33c to separate the support tube 13 from the camera unit 11. Next, the operator separates the support tube 13 from the camera unit 11 (which will be described later) and guides the camera unit 11, the camera-side cable 12, and the support tube 13 to the outside of the body through the trocar 32b. Here, the connector 15a of the camera-side cable 12 is temporarily returned into the body through the trocar 31 and is thereafter drawn out to the outside of the body through the trocar 32a or 32b.

Figure 14:
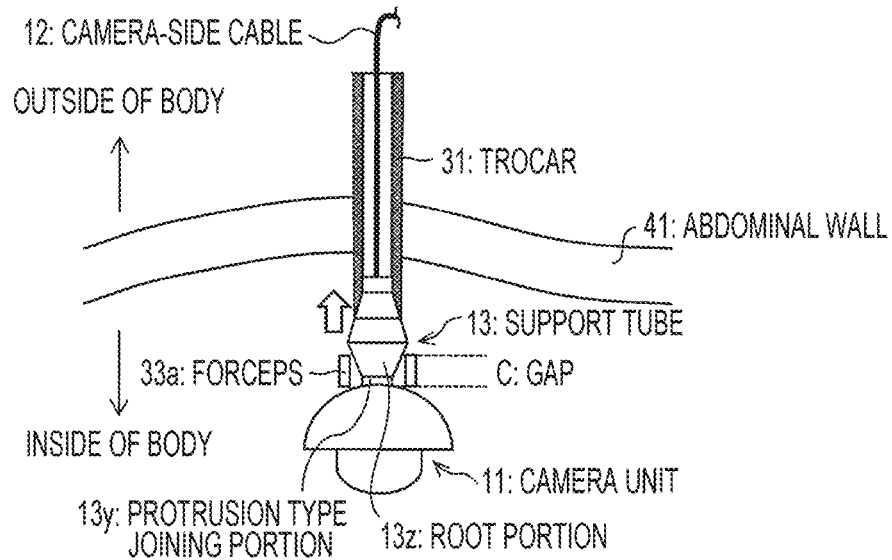
FIG. 14 is a side cross-sectional diagram (a) and a front cross-sectional diagram (b) that illustrate separation steps between the camera unit and the support tube in the first embodiment.
Figure 14:
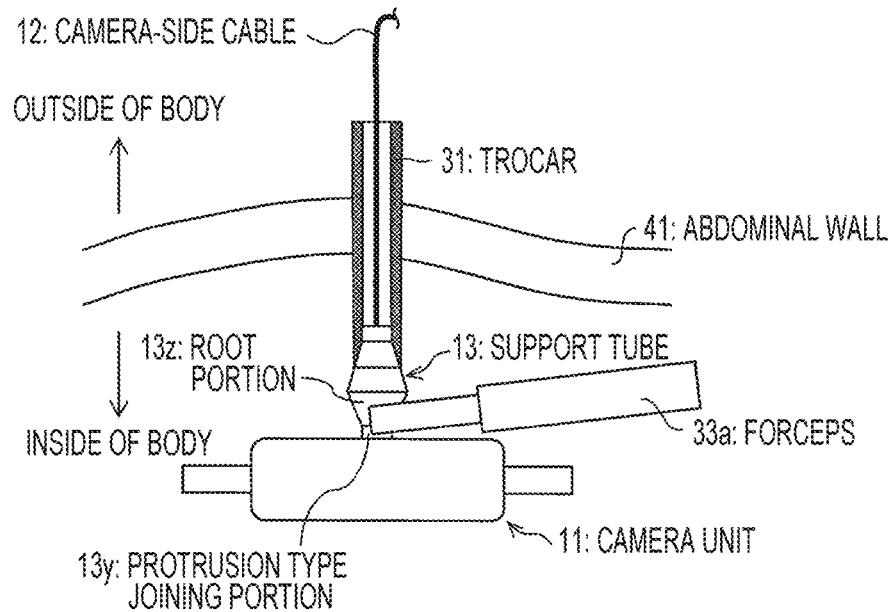

FIG. 14 is a side cross-sectional diagram (a) and a front cross-sectional diagram (b) that illustrate separation steps between the camera unit and the support tube in the first embodiment. In the support tube 13 in FIG. 11, because the root portion 13z is in a truncated conical shape, in a case where the support tube 13 is joined to the camera unit 11 as illustrated in (a) and (b) in FIG. 14, the gap C between the upper surface of the camera unit 11 and the outside surface of the root portion 13z becomes smaller as the gap C approaches the protrusion type joining portion 13y. Thus, the two tip ends of the forceps 33a are placed into the gap C, those are closed, the support tube 13 thereby moves upward, and the camera unit 11 may easily be separated from the support tube 13.

Figure 15:
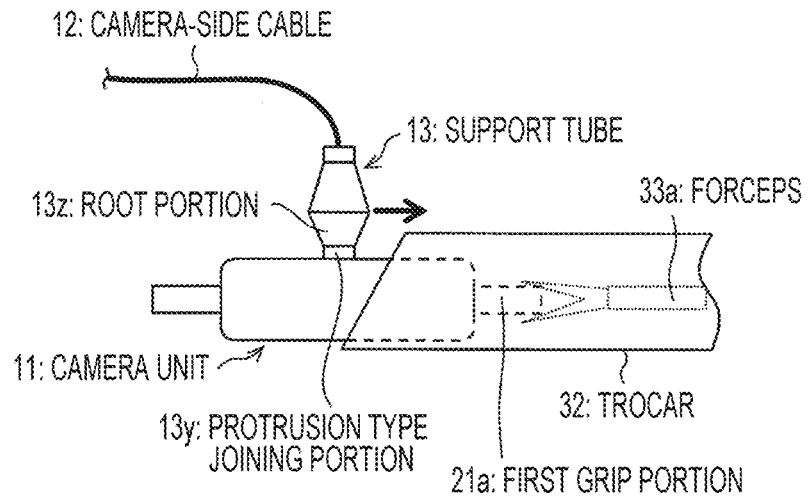
FIG. 15 is schematic diagrams (a) and (b) that illustrate other separation steps between the camera unit and the support tube in the first embodiment.
Figure 15:
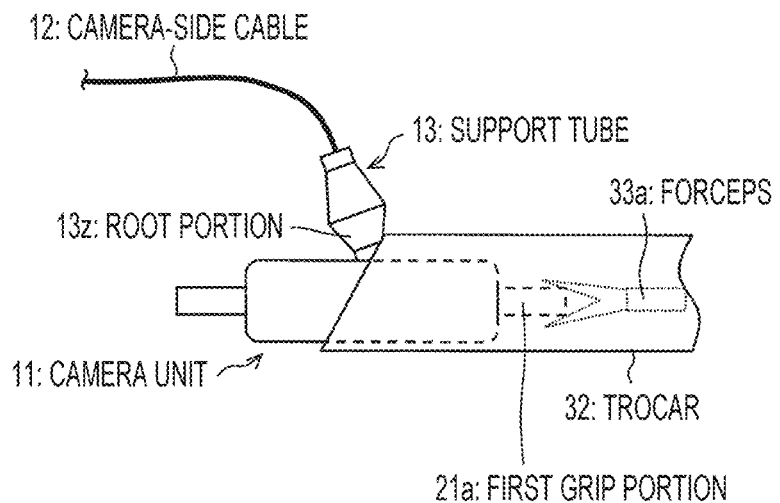

FIG. 15 is schematic diagrams (a) and (b) that illustrate other separation steps between the camera unit and the support tube in the first embodiment (a case where the support tube is removed from the trocar before the support tube is removed from the camera unit). First, as illustrated in (a) in FIG. 15, a trocar 32 (for example, the trocar 32b in FIGS. 12 and 13) used for inserting the forceps and the endoscope into the body is used for collection, the first grip portion 21a of the camera unit 11 is pinched by the forceps 33a, and the camera unit 11 is drawn into an internal portion of the trocar 32. Accordingly, simultaneously with a draw-out operation, the outside surface of the root portion 13z abuts (is caught) an opening of the collection trocar 32, an upward (the direction perpendicular to the upper surface of the camera unit 11) force is added to the support tube 13, and the support tube 13 may thereby be removed from the camera unit 11.

Figure 16:
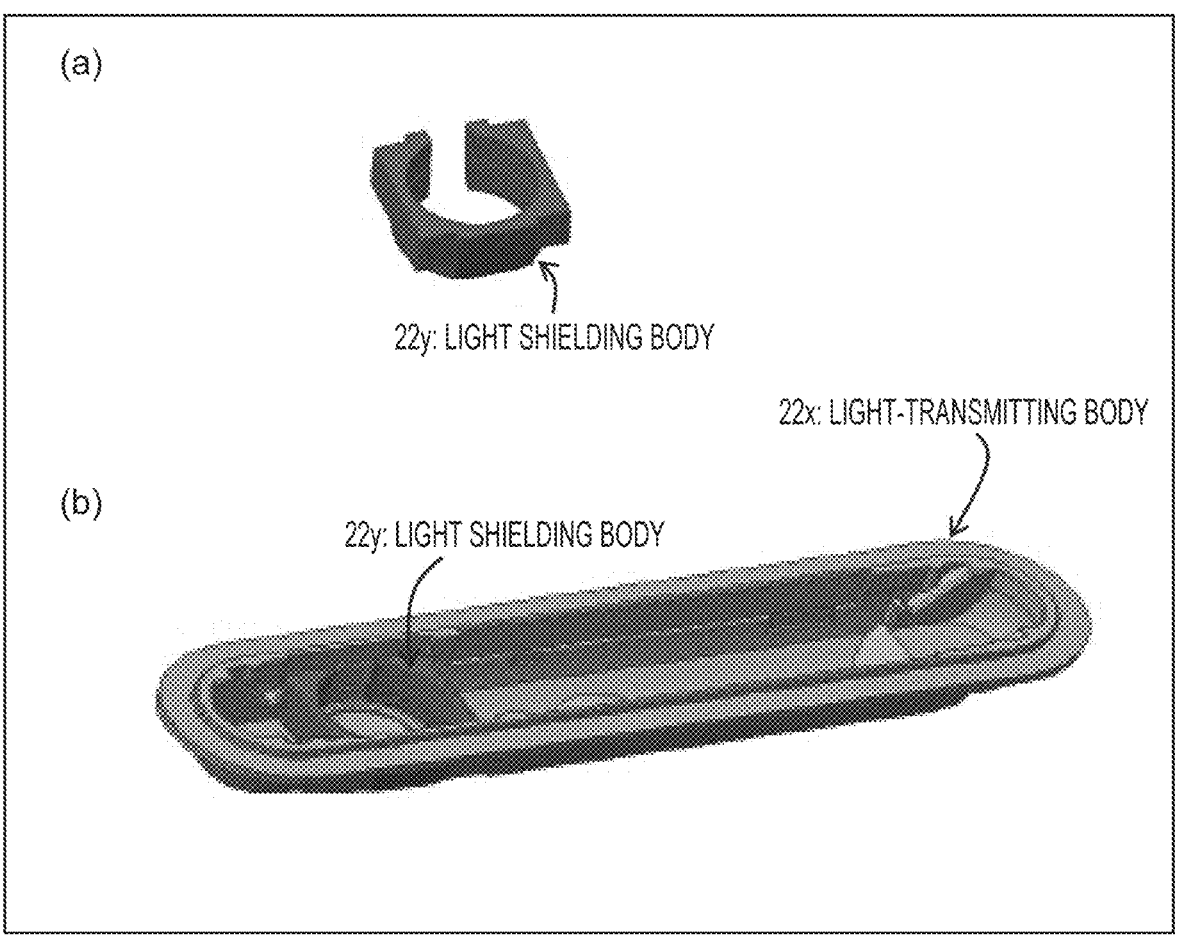
FIG. 16 is a perspective diagram (a) of the light shielding body and a perspective diagram (b) of the casing that illustrate another configuration of the casing of the first embodiment.

Note that in the configuration illustrated in FIG. 3 to FIG. 6, the laminated portion 22e is provided to the casing 22. However, embodiments are not limited to this. As illustrated in FIG. 16, only a portion that surrounds the lens may be formed with the light shielding body 22y.

Figure 17:
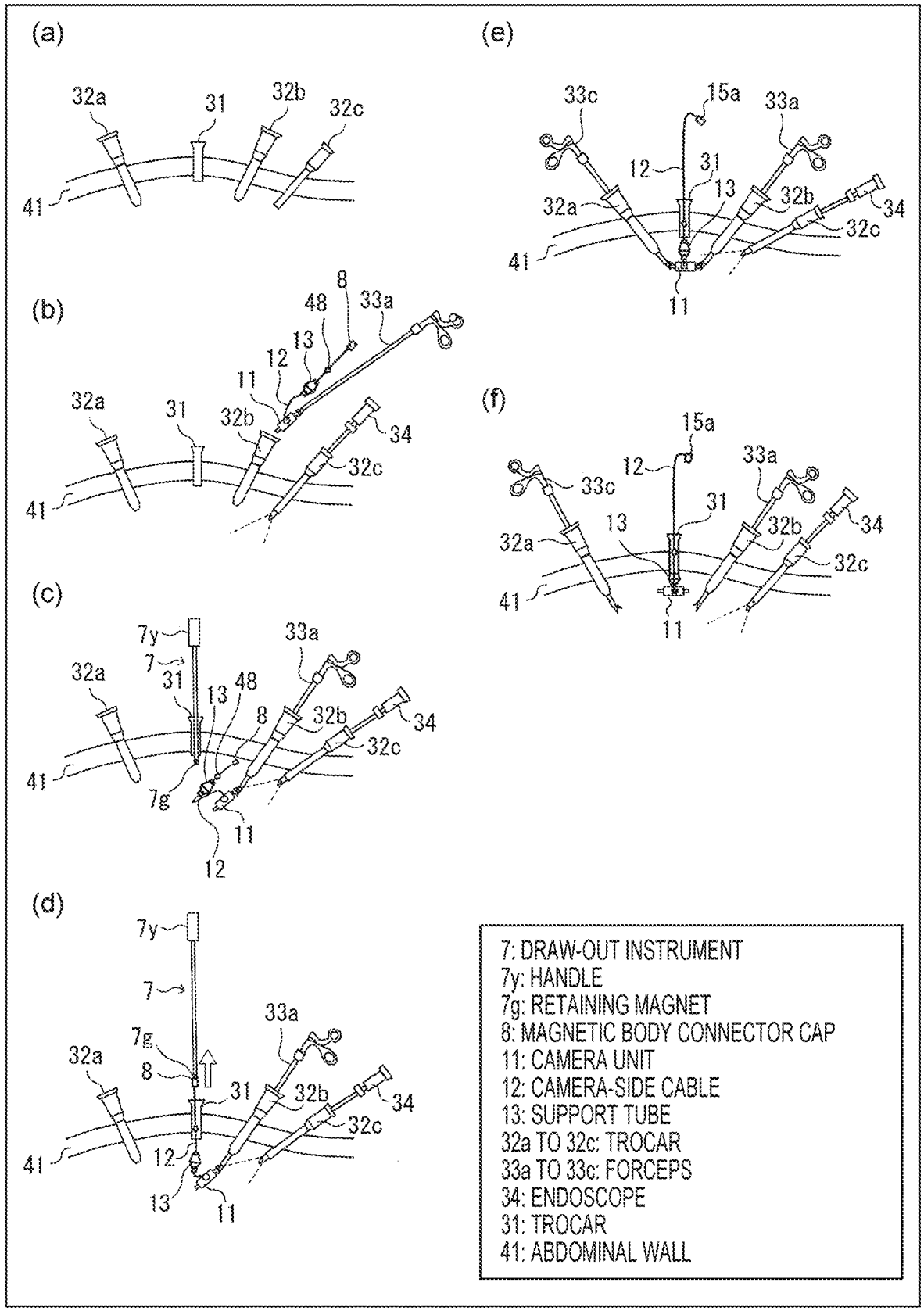
FIG. 17 is schematic diagrams (a) to (f) that illustrate use examples of the support tube, the camera unit, and the trocars in a second embodiment.

Second Embodiment (a) to (f) in FIG. 17 are schematic diagrams that illustrate an installation method of the camera unit in the body in a second embodiment. In the second embodiment, the camera-side cable connector 15a in FIG. 1 or the like is covered by a magnetic body connector cap 8 (a protection cap provided with a magnetic body at a tip end), and a draw-out instrument 7 that has a handle 7y at one end and has a retaining magnet 7g on the other end is used. Note that as the magnetic body of the magnetic body connector cap 8, a magnetic body that is not a magnet is used. This prevents the magnetic body connector cap 8 from being accidentally stuck to another metal treatment instrument, and work efficiency may thereby be enhanced.

As illustrated in (a) in FIG. 17, the operator first opens holes (ports) for inserting forceps and an endoscope in the body cavity in the abdominal wall 41 and inserts the trocars 32a to 32c in the ports. In addition, in order to install the camera unit 11 in the body cavity, the port is opened in a position in the abdominal wall 41 from which the whole organ including an affected site may be seen, and the trocar 31 is inserted therein.

Next, as illustrated in (b) in FIG. 17, the operator inserts the endoscope 34 in the body cavity through the trocar 32c and inserts the camera unit 11 grasped by the forceps 33a, the camera-side cable 12 that includes the camera-side cable connector 15a covered by the magnetic body connector cap 8, and the support tube 13 through which the camera-side cable 12 places in the body cavity through the trocar 32b while observing the inside of the body by using the endoscope 34.

Next, as illustrated in (c) in FIG. 17, the operator moves the camera unit 11 to the vicinity of the trocar 31 by operating the forceps 33a and inserts the draw-out instrument 7 in the body cavity through the trocar 31.

Next, as illustrated in (d) in FIG. 17, the draw-out instrument 7 is pulled out from the trocar 31 in a state where the magnetic body connector cap 8 is adhered to the retaining magnet 7g provided to a tip end of the draw-out instrument 7, and the camera-side cable connector that is covered by the magnetic body connector cap 8 is thereby guided to the outside of the body. Here, the camera unit 11 (the grip portion thereof) is grasped by the forceps 33a.

Next, as illustrated in (e) in FIG. 17, the operator draws up the camera-side cable 12 guided to the outside of the body by forceps, the hand, or the like and thereby brings the tip end of the support tube 13 to proximity of the opening of the trocar 31.

Next, as illustrated in (f) in FIG. 17, the operator further draws up the camera-side cable 12 and the camera unit 11, thereby inserts one end (trocar connection portion) of the support tube 13 into the end portion of the trocar 31 on the inside of the body, fits the camera unit 11 in the other end (protrusion type joining portion), thereby connects the one end (trocar connection portion) of the support tube 13 with the end portion of the trocar 31 on the inside of the body, joins the other end (protrusion type joining portion) to the camera unit 11, and thereby fixes the camera-side cable 12 to the abdominal wall 41 or the like such that the tension of the camera-side cable 12 is maintained.

In the second embodiment, in a case where the camera-side cable connector 15a covered by the magnetic body connector cap 8 is drawn out to the outside of the body by using the draw-out instrument 7, if the support tube 13 is in the vicinity of the trocar 31, the support tube 13 enters the opening of the trocar 31 before the magnetic body connector cap 8 passes through the inside of the trocar 31 (before the operator pinches the magnetic body connector cap 8). Thus, it is possible that the magnetic body connector cap 8 is separated from the retaining magnet 7g due to the friction.

Figure 18:
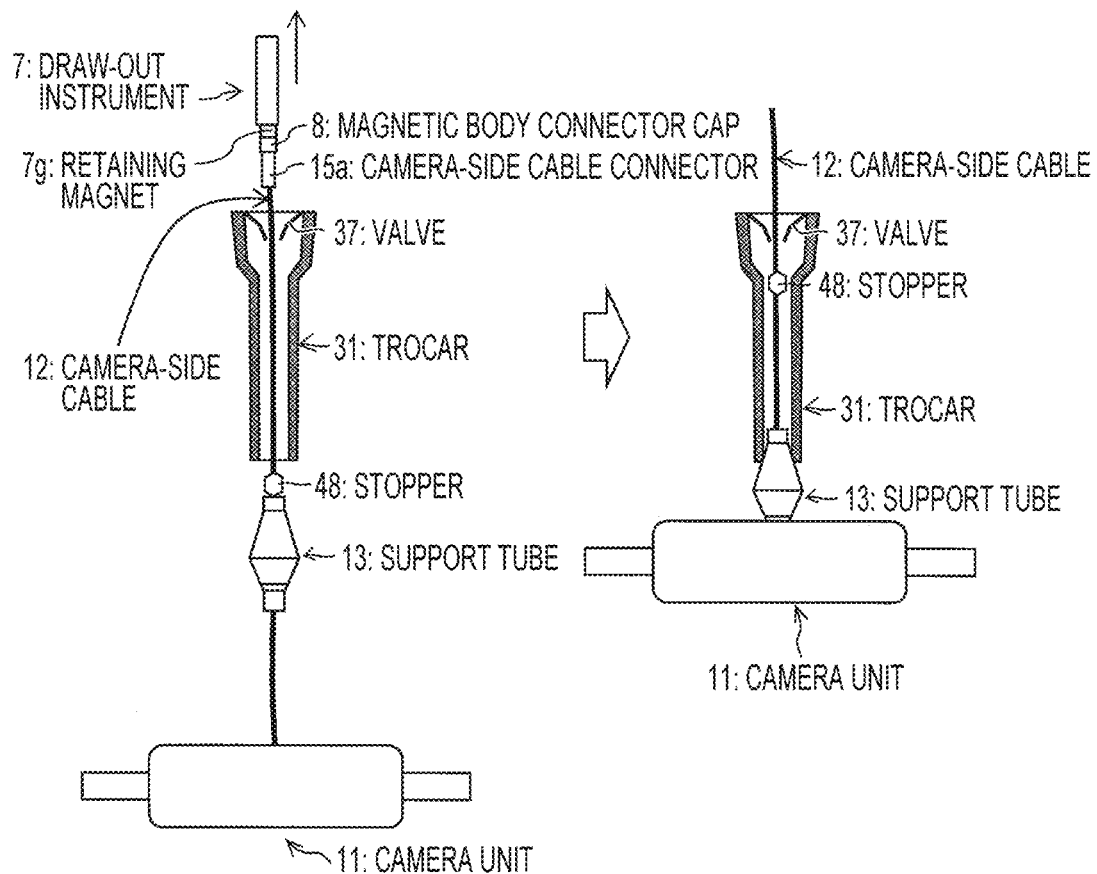
FIG. 18 is schematic diagrams (a) to (c) that illustrate installation examples of the support tube, a stopper, the camera unit, and the trocar in the second embodiment.

Thus, as in (a) in FIG. 18, the stopper 48 that stops movement of the support tube 13 toward the connector 15a side is desirably provided between the camera unit 11 and the camera-side cable connector 15a. Accordingly, as in (b) and (c) in FIG. 18, because the support tube 13 enters the opening of the trocar 31 after the magnetic body connector cap 8 passes through the inside of the trocar 31 (after the operator pinches the magnetic body connector cap 8), the installation of the camera unit 11 may be performed smoothly.

Here, in a case where the support tube 13 of the first embodiment is used, the stopper 48 desirably has a shape that may pass through the inside of the insertion hole D of the attachment 13b. For example, the outer diameter of the stopper 48 is set smaller than the minimum hole diameter of the insertion hole D of the attachment 13b. Accordingly, the manufacture of the support tube 13 may be simplified.

Further, as illustrated in (c) in FIG. 18, the stopper 48 is positioned such that the stopper 48 does not reach a valve 37 of the trocar 31 when the installation is completed, and the camera unit 11 may thereby be installed more smoothly.

Third Embodiment

Figure 19:
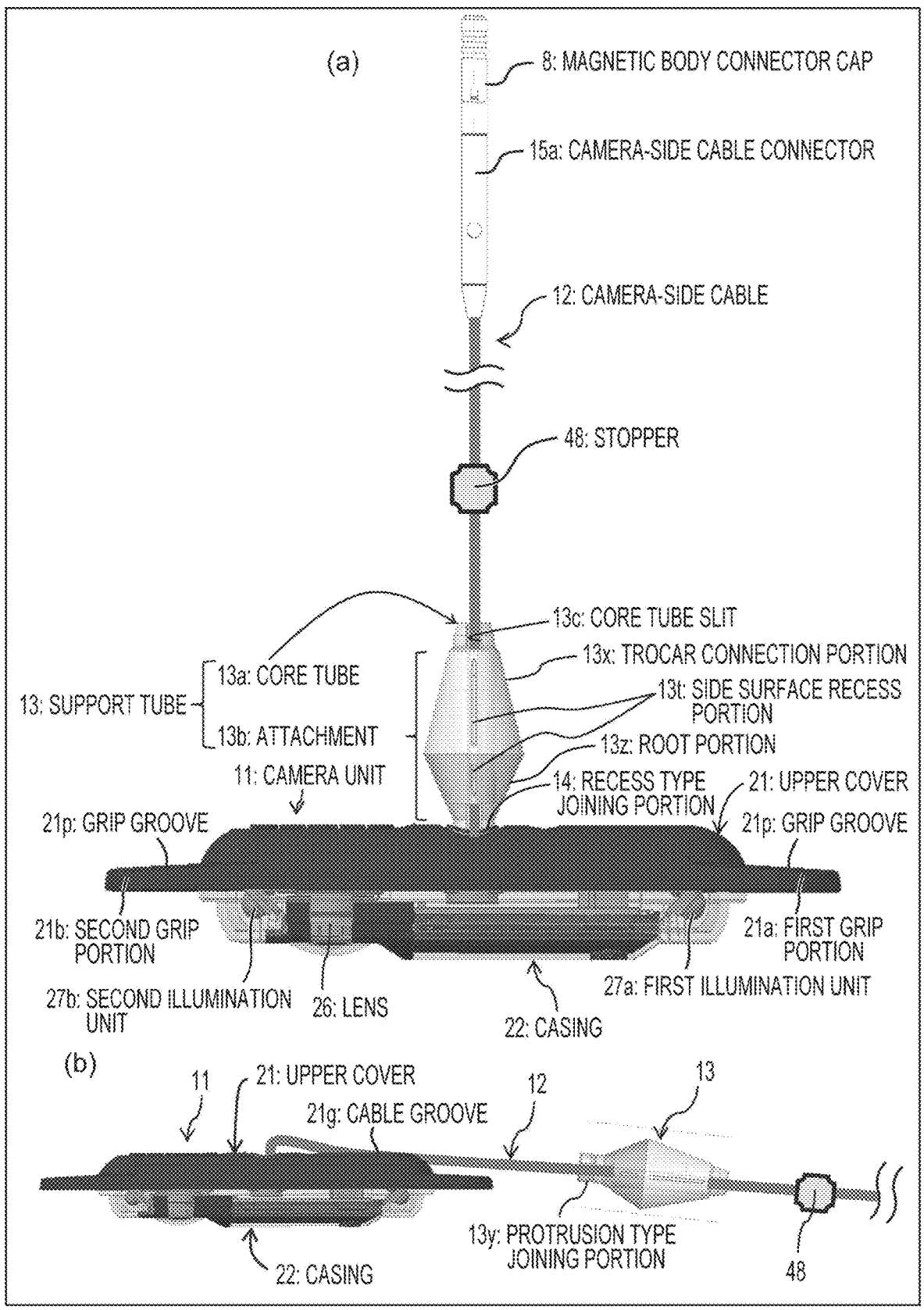
FIG. 19 is front diagrams (a) and (b) that illustrate installation examples of the camera unit, the support tube, the stopper, and the camera-side cable in a third embodiment.
Figure 20:
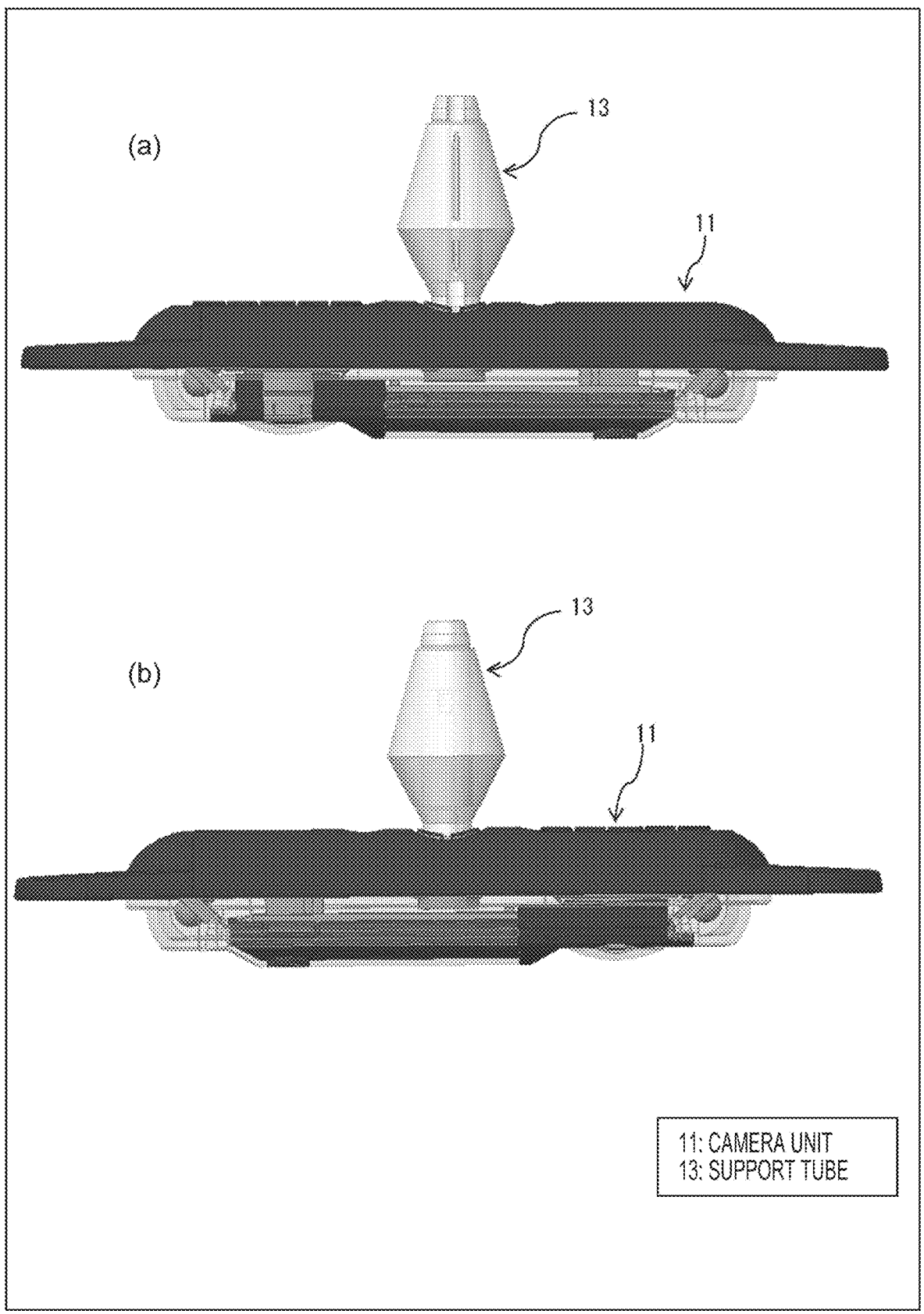
FIG. 20 is a front diagram (a) and a back diagram (b) that illustrate installation examples of the camera unit and the support tube in the third embodiment.
Figure 21:
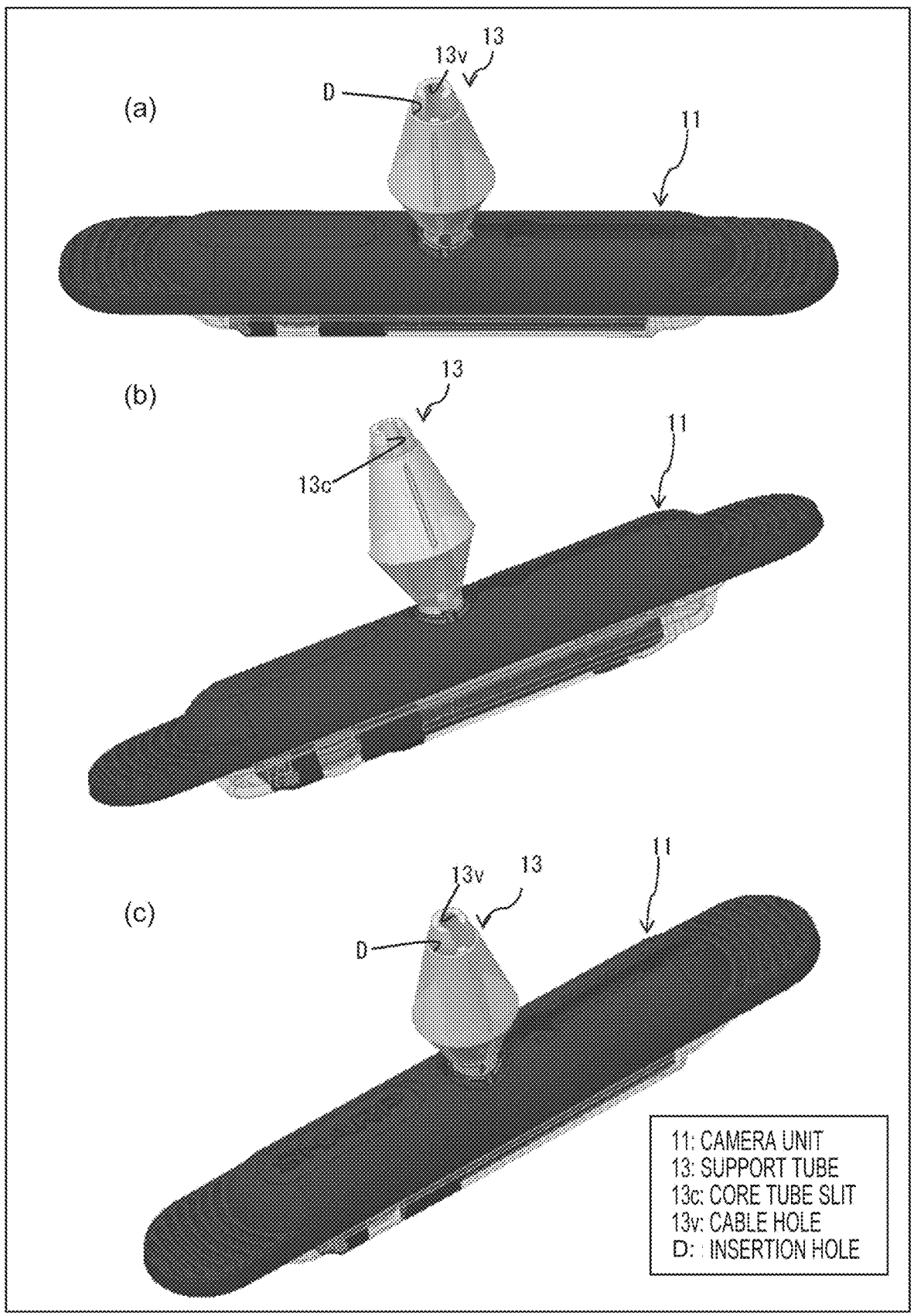
FIG. 21 is perspective diagrams (a) to (c), as seen from an upper side, which illustrate installation examples of the camera unit and the support tube in the third embodiment.
Figure 22:
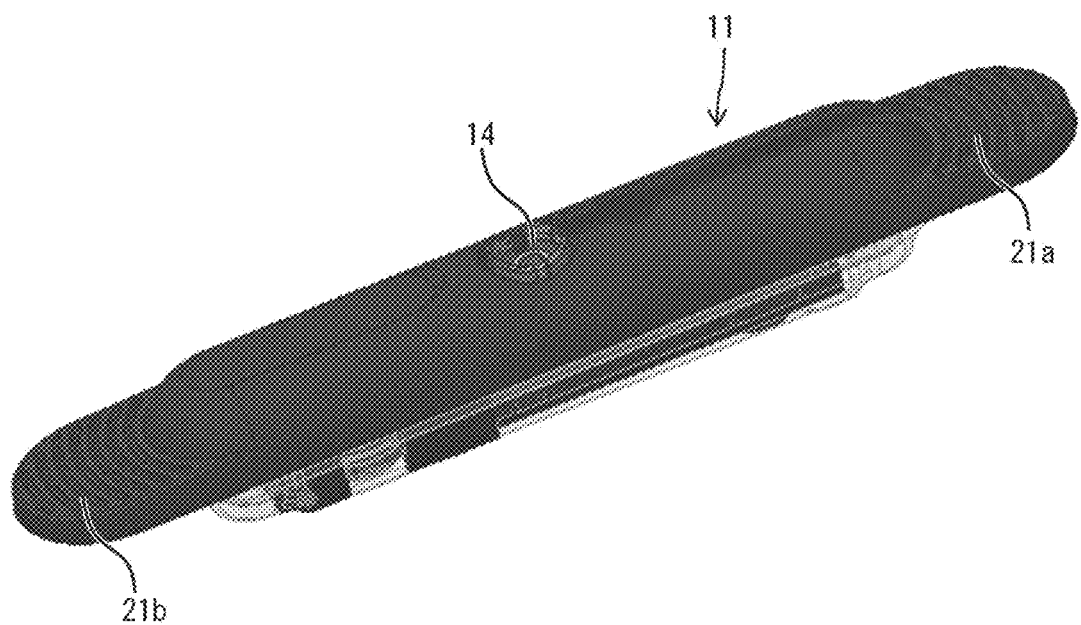
FIG. 22 is a perspective diagram of the camera unit in the third embodiment as seen from an upper side.
Figure 23:
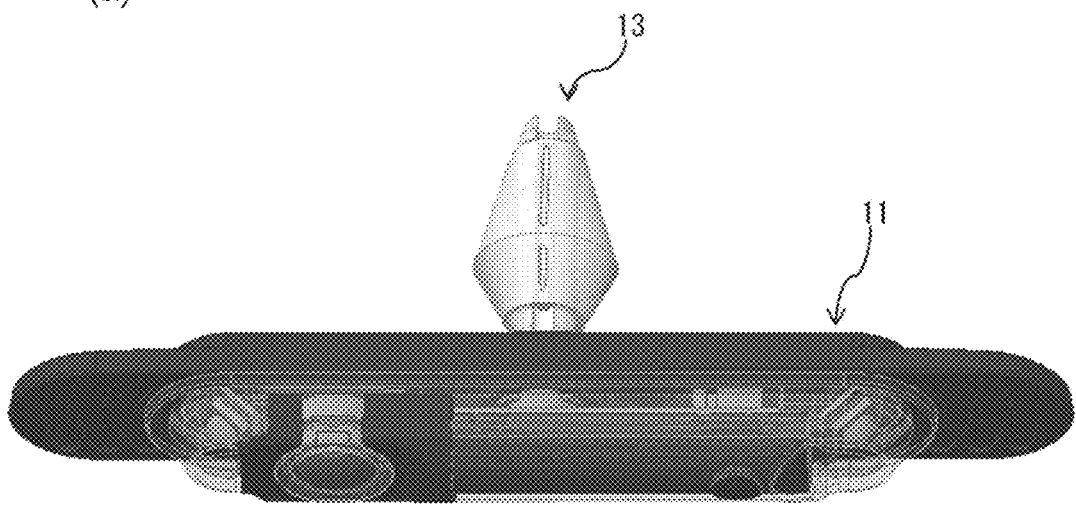
FIG. 23 is perspective diagrams (a) and (b), as seen from a lower side, which illustrate installation examples of the camera unit and the support tube in the third embodiment.
Figure 23:
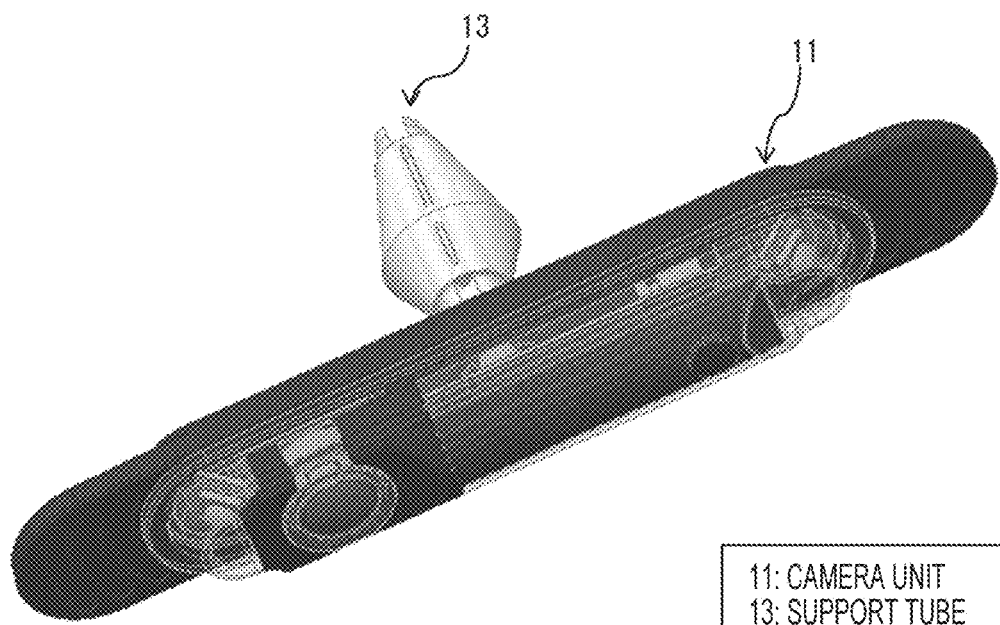
Figure 24:
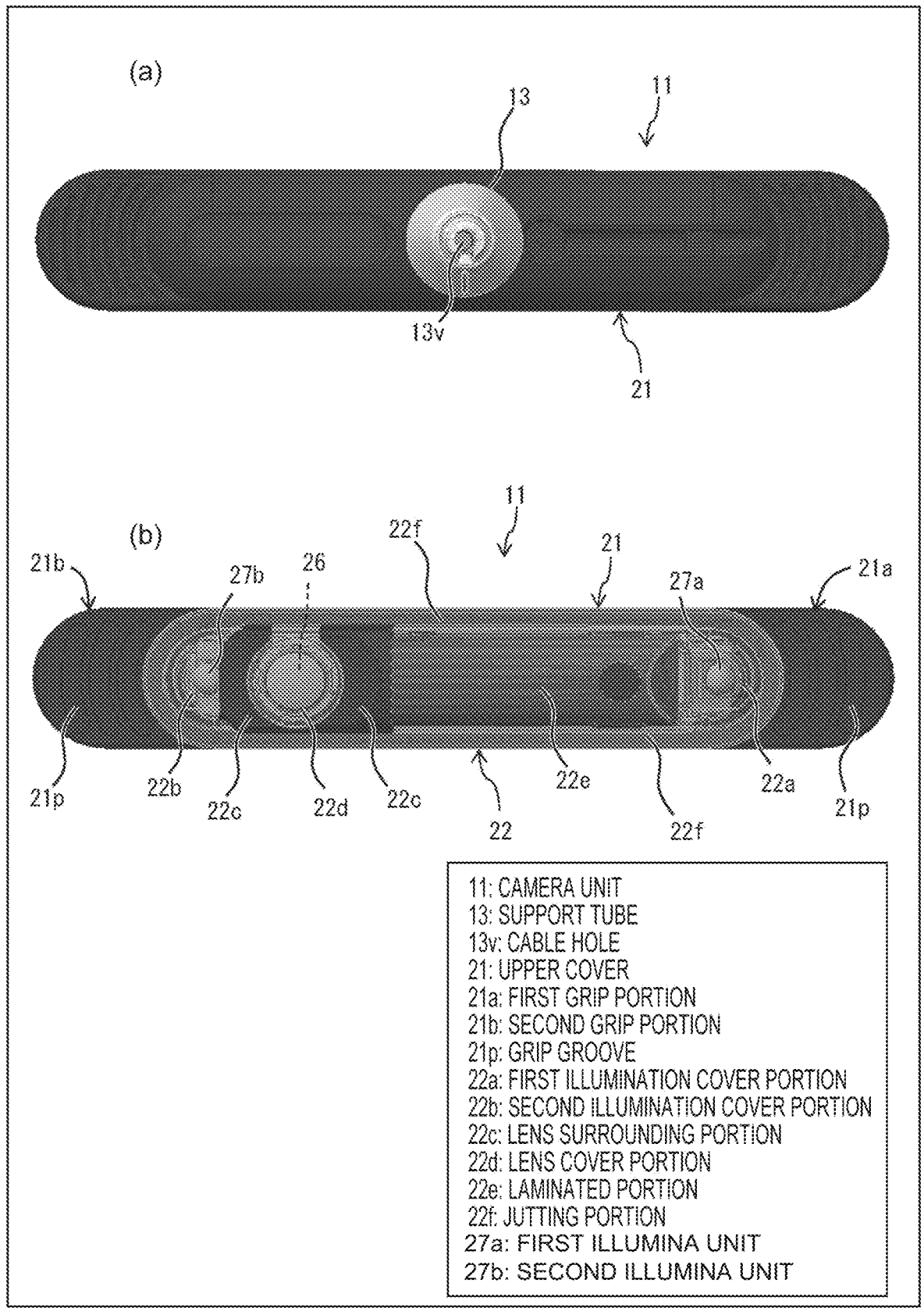
FIG. 24 is a top diagram (a) and a bottom diagram (b) that illustrate installation examples of the camera unit and the support tube in the third embodiment.
Figure 25:
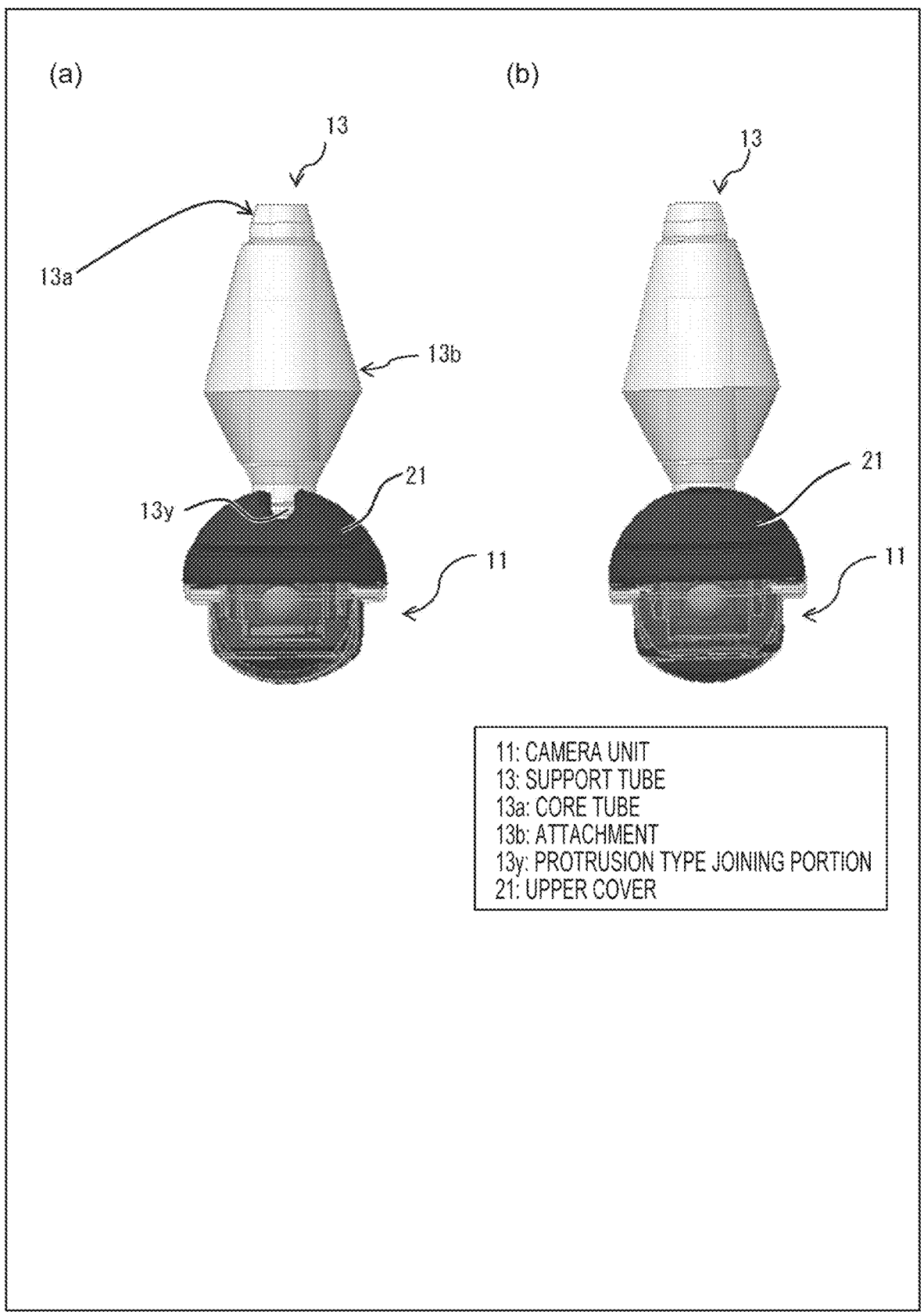
FIG. 25 is a right side diagram (a) and a left side diagram (b) that illustrate installation examples of the camera unit and the support tube in the third embodiment.

FIG. 19 is front diagrams (a) and (b) that illustrate installation examples of the camera unit, the support tube, the stopper, and the camera-side cable in a third embodiment. FIG. 20 is a front diagram (a) and a back diagram (b) that illustrate installation examples of the camera unit and the support tube in the third embodiment. FIG. 21 is perspective diagrams (a) to (c), as seen from an upper side, which illustrate installation examples of the camera unit and the support tube in the third embodiment. FIG. 22 is a perspective diagram of the camera unit in the third embodiment as seen from an upper side. FIG. 23 is perspective diagrams (a) and (b), as seen from a lower side, which illustrate installation examples of the camera unit and the support tube in the third embodiment. FIG. 24 is a top diagram (a) and a bottom diagram (b) that illustrate installation examples of the camera unit and the support tube in the third embodiment. FIG. 25 is a right side diagram (a) and a left side diagram (b) that illustrate installation examples of the camera unit and the support tube in the third embodiment.

As illustrated in FIG. 19 and FIG. 21, the support tube 13 is configured with the core tube 13a that has the cable hole 13v (circular opening) and the attachment 13b that is attached to the outside surface of the core tube 13a. The core tube slit 13c that longitudinally crosses the core tube 13a from one opening to the other opening of the core tube 13a is formed in the core tube 13a. The hole diameter (the inner diameter of the support tube 13) of the cable hole 13v is smaller than the outer diameter of the camera-side cable connector.

As illustrated in FIG. 19 and FIG. 21, the attachment 13b is in a spindle shape that has the insertion hole D and is formed with the trocar connection portion 13x in a truncated conical shape that becomes thinner in the direction to separate from the camera unit 11 and the root portion 13z in a truncated conical shape that becomes thinner in the direction to approach the camera unit 11. Note that the taper angle of the root portion 13z is larger than the taper angle of the trocar connection portion 13x.

Further, the support tube 13 is configured by fitting the core tube 13a in the insertion hole D of the attachment 13b and thereby mounting the attachment 13b on the core tube 13a. Note that side surface recess portions 13t that overlap with the core tube slit 13c are provided to respective portions of the trocar connection portion 13x and the root portion 13z on a side surface of the attachment 13b.

Although not illustrated, a locking claw is provided on the inside of the attachment 13b, and a locking hole is provided in the position that is on the opposite side to the core tube slit 13c in the core tube 13a. Further, a guide claw of the attachment 13b is caused to match the position of the core tube slit 13c, and the locking hole is thereby fitted on the locking claw. As marks that indicate the guide claw, the side surface recess portions 13t are provided.

Here, the attachment 13b is configured such that the camera-side cable connector 15a may be placed through the inside of the insertion hole D. Specifically, the minimum hole diameter of the insertion hole D of the attachment 13b is set larger than the outer diameter of the camera-side cable connector 15a. However, embodiments are not limited to this construction. Even in a case where the minimum hole diameter of the insertion hole D of the attachment 13b is smaller than the outer diameter of the camera-side cable connector 15a, it is sufficient that the camera-side cable connector 15a may be placed through the inside of the insertion hole D by changing the orientation of the camera-side cable connector 15a. Further, it is also sufficient that the camera-side cable connector 15a may be placed through the inside of the insertion hole D by deforming the attachment 13b (changing the shape of the insertion hole D).

Further, the camera-side cable 12 has the stopper 48 that stops movement of the support tube 13 toward the connector 15a side between the connection end with the camera unit 11 and the camera-side cable connector 15a. The stopper 48 is configured to be capable of passing through the inside of the insertion hole D of the attachment 13b but not capable of passing through the inside of the core tube 13a. For example, the outer diameter of the stopper 48 is set smaller than the minimum hole diameter of the insertion hole D of the attachment 13b and larger than the minimum hole diameter of the cable hole 13v of the core tube 13a.

Further, the camera-side cable 12 that has the camera-side cable connector 15a and the stopper 48 is placed through the inside of the support tube 13 from the core tube slit 13c, the camera-side cable connector 15a and the stopper 48 are further placed through the inside of the insertion hole D (see FIG. 21) of the attachment 13b, the attachment 13b is mounted on the outside surface of the core tube 13a, and both of those are adhered together. The camera-side cable connector 15a is thereafter covered by the magnetic body connector cap 8. Note that as illustrated in (d) in FIG. 17, in the installation of the camera unit 11 in the body, in a state where the magnetic body connector cap 8 is retained by the retaining magnet 7g of the draw-out instrument 7, the camera-side cable connector 15a with the magnetic body connector cap 8 is caused to pass through an internal portion of the tubular tool (for example, the trocar 31 in FIG. 17) and is drawn out from the end portion of the tubular tool on the outside of the body to the outside.

Note that as illustrated in (b) in FIG. 19 and FIG. 25, in the core tube 13a, the lower portion (the end portion on the camera unit 11 side) on which the attachment 13b is not mounted serves as the protrusion type joining portion 13y.

Note that on a side surface of the attachment 13b, an opening, a full slit (a longitudinally crossing slit that is from one end and reaches the other end), or a partial slit (a slit that does not reach the other end) may be provided.

As illustrated in FIGS. 19 and 20, the camera unit 11 is formed into a ship shape that is easily placed through the tubular tool, and the image capturing unit (including the lens 26 and the image sensor that is not illustrated), the circuit substrate and the control circuit that are not illustrated, and the first and second illumination units 27a and 27b are housed between the upper cover 21 and the casing 22.

The casing 22 has a thin-long shape, and the first and second illumination units 27a and 27b are arranged in the two end portions (tip end portions) in the longitudinal direction.

The upper cover 21 has a thin-long shape, two end portions (tip end portions) in the longitudinal direction form the first and second grip portions 21a and 21b, and the recess type joining portion 14 is formed in a central portion. The first and second grip portions 21a and 21b are in a flat-plate shape, and plural finger-print-like recesses for preventing slip are formed in each of the upper surfaces and lower surfaces. Further, the upper cover 21 curves so as to be protruded upward (toward the opposite side to the casing 22).

The casing 22 has a light-transmitting portion and a light shielding portion. In a bottom view in (b) in FIG. 24, the first illumination unit 27a is provided in the vicinity of a first grip portion 21a, the second illumination unit 27b is provided in the vicinity of a second grip portion 21b, and the lens 26 is provided between the first and second illumination units 27a and 27b.

As illustrated in FIG. 19 and (b) in FIG. 25, the casing 22 is integrally molded with an integral light-transmitting body and an integral light shielding body and includes the first illumination cover portion 22a that covers the first illumination unit 27a, the second illumination cover portion 22b that covers the second illumination unit 27b, the lens surrounding portion 22c that surrounds the lens 26, the lens cover portion 22d that covers the lens 26, and the jutting portion 22f that juts outward from the vicinity of the opening of the casing 22. The first and second illumination cover portions 22a and 22b, the lens cover portion 22d, and the jutting portion 22f are configured with the light-transmitting body, and the lens surrounding portion 22c is configured with the light shielding body. The casing 22 further includes the laminated portion 22e whose outside is configured with the light-transmitting body and whose inside is configured with the light shielding body between the first illumination cover portion 22a and the lens surrounding portion 22c.

Note that in a case where the camera unit 11 is collected, because the camera-side cable connector 15a in a state where the magnetic body connector cap 8 is removed is temporarily returned to the inside of the body, the camera-side cable connector 15a has to be maintained in a clean state from the beginning to the end of surgery. Meanwhile, in view of easiness of use for the operator, it is desirable that the camera-side cable connector 15a and the magnetic body connector cap 8 are accommodated in a sterile bag in a state where the magnetic body connector cap 8 is fitted on the camera-side cable connector 15a (the state in FIG. 19) and are in a state where those are ready for immediate use when the sterile bag is opened. In order to do so, gas sterilization is requested to be feasible to an internal portion of the magnetic body connector cap 8 while the magnetic body connector cap 8 is kept fitted on the camera-side cable connector 15a.

Accordingly, at least a portion of the magnetic body connector cap 8 is desirably configured with a fine filter material that allows sterilization gas to pass but does not allow at least liquids such as water and body fluids to pass and, if possible, does not allow bacteria or the like to pass.

[Conclusion]

As described in the foregoing, an in-body image capturing device according to a first aspect of the present invention includes an image capturing unit that includes a lens, and an illumination unit, the in-body image capturing device being capable of being introduced into a body, and the image capturing unit and the illumination unit are housed in a casing that is integrally molded with an integral light-transmitting body and an integral light shielding body.

In the above configuration, the illumination unit and the image capturing unit are housed in the casing that is integrally molded with the integral light-transmitting body and the integral light shielding body. Thus, an adverse influence of internal stray light is suppressed, and air-tightness and mechanical strength are enhanced. Consequently, an in-body image capturing device with high reliability may be realized.

As for the in-body image capturing device according to a second aspect of the present invention, in the first aspect, the casing includes an illumination cover portion that covers the illumination unit, a lens cover portion that covers the lens, and a lens surrounding portion that surrounds the lens, the illumination cover portion and the lens cover portion are configured with the light-transmitting body, and the lens surrounding portion is configured with the light shielding body.

In such a manner, the lens and the illumination unit are not exposed to the outside, and reliability may thereby be enhanced.

As for the in-body image capturing device according to a third aspect of the present invention, in the second aspect, the lens surrounding portion is configured to have a light shielding wall that is positioned between the lens and the illumination unit.

In the above configuration, an adverse influence on image capturing by the stray light in an internal portion of the casing may be reduced.

As for the in-body image capturing device according to a fourth aspect of the present invention, in the second aspect, the casing is configured to include a laminated portion in which the light-transmitting body and the light shielding body are laminated between the illumination cover portion and the lens surrounding portion.

In such a manner, the laminated portion is provided whose outside is configured with the light-transmitting body and whose inside is configured with the light shielding body, and the mechanical strength of the casing may thereby be enhanced.

As for the in-body image capturing device according to a fifth aspect of the present invention, in any one of the first to fourth aspects, the casing is configured to include a jutting portion that juts outward from a vicinity of an opening of the casing, and the jutting portion is configured with the light-transmitting body.

In the above configuration, the jutting portion may be used as a margin for laser welding, and the air-tightness and mechanical strength of the casing may thereby be enhanced.

As for the in-body image capturing device according to a sixth aspect of the present invention, in any one of the first to fourth aspects, a light irradiation direction (direction in which the light amount becomes the maximum) of the illumination unit is configured to be inclined in a direction to separate from the lens with respect to an optical axis direction of the lens.

In such a manner, the illumination unit is inclined, and the adverse influence on the image capturing by the stray light in the internal portion of the casing may thereby be reduced.

As for the in-body image capturing device according to a seventh aspect of the present invention, in the second aspect, emboss processing (processing for providing protrusions and recesses on a surface, for example, a sandblasting process or a beading process) is configured to be applied to an internal surface of the illumination cover portion.

In the above configuration, light scattering by the illumination cover portion increases, and the adverse influence on the image capturing by the stray light in the internal portion of the casing may thereby be reduced.

As for the in-body image capturing device according to an eighth aspect of the present invention, in the sixth aspect, in the casing, another illumination unit is configured to be housed in a position on an opposite side to the illumination unit with respect to the lens, and a light irradiation direction of the other illumination unit is configured to be inclined in a direction to separate from the lens with respect to the optical axis direction of the lens.

In such a manner, the other illumination unit is inclined, and the adverse influence on the image capturing by the stray light in the internal portion of the casing may thereby be reduced.

As for the in-body image capturing device according to a ninth aspect of the present invention, in the eighth aspect, the light irradiation direction of each of the illumination unit and the other illumination unit is configured to be inclined at 30° to 70° (more preferably 45°) with respect to a lens optical axis.

As for the in-body image capturing device according to a tenth aspect of the present invention, in the second aspect, the lens cover portion is configured to be protruded to an outside of the casing.

In the above configuration, a wide image capturing angle may be realized. Further, even in a case where dirt sticks on the lens cover portion in surgery, it is easy for an operator to wipe the dirt by gauze or the like pinched between forceps.

As for the in-body image capturing device according to an eleventh aspect of the present invention, in the fifth aspect, the in-body image capturing device is configured to further include a light shielding upper cover that covers the opening of the casing, and the upper cover and the jutting portion are configured to be laser-welded together.

In such a manner, the jutting portion and the upper cover are laser-welded together, and the air-tightness and mechanical strength of the casing may thereby be enhanced.

As for the in-body image capturing device according to a twelfth aspect of the present invention, in any one of the first to tenth aspects, the in-body image capturing device is configured to further include an upper cover that covers an opening of the casing, and a cable that is electrically connected with the illumination unit and the image capturing unit and is drawn out to an outside from the upper cover.

In the above configuration, connection between the in-body image capturing device and an external apparatus (such as the tubular tool) becomes easy.

As for the in-body image capturing device according to a thirteenth aspect of the present invention, in any one of the first to tenth aspects, the in-body image capturing device is configured to further include an upper cover that covers an opening of the casing, the upper cover is configured to be in an elongated shape, and at least one of both end portions of the upper cover is configured to be formed as a grip portion.

In the above configuration, it becomes easy to grip the in-body image capturing device.

As for the in-body image capturing device according to a fourteenth aspect of the present invention, in the thirteenth aspect, a groove is configured to be formed in at least one of an upper surface and a lower surface of the grip portion.

In the above configuration, the groove provides an effect of preventing slip, and it becomes easier to grip the in-body image capturing device.

An in-body monitoring camera system includes the in-body image capturing device according to any one of the first to fourteenth aspects, a support tube that has a connection portion with a tubular tool which is capable of being introduced into the body on one end side and has a joining portion to the in-body image capturing device on another end side, a cable that is connected with the in-body image capturing device and passes through the support tube, and a control system that is electrically connected with the cable and includes at least a display device.

In the above configuration, the supporting force for the in-body image capturing device is enhanced, connection failure of the cable is less likely to occur, and reliability is improved. Further, an operator may change the orientation of the image capturing portion in the body by operating the tubular tool, and easiness of use is thereby improved.

The present invention includes an in-body image capturing device that includes an image capturing unit, a casing which houses the image capturing unit, and an upper cover which covers an opening of the casing and that is capable of being introduced into a body, in which at least one of two end portions of the upper cover, which face each other, is formed as a grip portion, and a groove is formed in at least one of an upper surface or a lower surface of the grip portion. The groove desirably extends in a curve shape or a polygonal line shape.

The present invention includes an in-body monitoring camera system that includes an in-body image capturing device which is capable of being introduced into a body, a cable whose one end is connected with the in-body image capturing device and whose other end has a connector, and a cap which covers the connector, in which a filter portion is provided to the cap. The filter portion desirably allows sterilization gas to pass but does not allow liquids such as water and body fluids (and bacteria or the like if possible) to pass.

The in-body image capturing device according to the present invention is applicable not only to in-body monitoring type cameras but also to capsule endoscopes that are caused to move in a body.

The present invention is not limited to the above embodiments. Modes that are the above embodiments appropriately changed or obtained by combining those based on common general technical knowledge are also included in embodiments of the present invention.

REFERENCE SIGNS LIST

1 in-body monitoring camera system
8 magnetic body connector cap 11 camera unit (in-body image capturing device)
12 camera-side cable (cable)
13 support tube
13x trocar connection portion
13y protrusion type joining portion
13a core tube
13b attachment
13c core tube slit
14 recess type joining portion
15a camera-side cable connector
15b apparatus-side cable connector
16 apparatus-side cable
21 upper cover
21a, 21b first and second grip portions
21p grip groove
22 casing
22x light-transmitting body
22y light shielding body
22a, 22b first and second illumination cover portions
22c lens surrounding portion
22d lens cover portion
22e laminated portion
22f jutting portion
31 trocar (tubular tool)
48 stopper

The invention claimed is:

1. A method of manufacturing an in-body image capturing device, the method comprising:
providing an image capturing unit that includes a lens and an illumination unit, the in-body image capturing device being capable of being introduced into a body;
integrally molding a casing with a light-transmitting body and a light shielding body by fitting, in an interior of a die of a whole of the casing, the light shielding body that has been molded in advance and pouring a transparent resin into gaps in the die, or by, in one molding machine, pouring a black resin into an interior of a die of the light shielding body, hardening the black resin, setting, in a die of a whole of the casing, the black resin thus hardened, and pouring the transparent resin into the die of the whole of the casing; and
housing the image capturing unit and the illumination unit in the casing, wherein
the light-transmitting body includes an illumination cover portion that covers the illumination unit and a lens cover portion that covers the lens, and
the light shielding body includes a lens surrounding portion that surrounds the lens.

2. The method of manufacturing the in-body image capturing device according to claim 1, wherein the lens surrounding portion has a light shielding wall that is positioned between the lens and the illumination unit.

3. The method of manufacturing the in-body image capturing device according to claim 1, wherein the casing includes a laminated portion in which a portion of the light-transmitting body and a portion of the light shielding body are laminated.

4. The method of manufacturing the in-body image capturing device according to claim 1, wherein the light-transmitting body includes a jutting portion that juts outward from a vicinity of an opening of the casing.

5. The method of manufacturing the in-body image capturing device according to claim 4, further comprising:
covering the opening of the casing with a light shielding upper cover, wherein
the upper cover and the jutting portion are laser-welded together.

6. The method of manufacturing the in-body image capturing device according to claim 1, wherein a light irradiation direction of the illumination unit is angled in a direction that diverges from a direction of an optical axis of the lens.

7. The method of manufacturing the in-body image capturing device according to claim 6, further comprising:
housing another illumination unit in the casing in a position on an opposite side to the illumination unit with respect to the lens, wherein
a light irradiation direction of the other illumination unit is angled in a direction that diverges from a direction of the optical axis of the lens.

8. The method of manufacturing the in-body image capturing device according to claim 7, wherein the light irradiation direction of each of the illumination unit and the other illumination unit is inclined at 30° to 70° with respect to a lens optical axis.

9. The method of manufacturing the in-body image capturing device according to claim 1, further comprising emboss processing an internal surface of the illumination cover portion.

10. The method of manufacturing the in-body image capturing device according to claim 1, wherein the lens cover portion is protruded to an outside of the casing.

11. The method of manufacturing the in-body image capturing device according to claim 1, further comprising:
covering an opening of the casing with an upper cover; and
electrically connecting a cable with the illumination unit and the image capturing unit and drawing the cable out to an outside from the upper cover.

12. The method of manufacturing the in-body image capturing device according to claim 1, further comprising:
covering an opening of the casing with an upper cover, wherein
the upper cover is in an elongated shape, and at least one of both end portions of the upper cover is formed as a grip portion.

13. The method of manufacturing the in-body image capturing device according to claim 12, further comprising forming a groove in at least one of an upper surface and a lower surface of the grip portion.

14. A method of manufacturing an in-body monitoring camera system, the method comprising:
manufacturing the in-body image capturing device according to the method of claim 1;
providing a support tube that has a connection portion with a tubular tool which is capable of being introduced into the body on one end side and has a joining portion to the in-body image capturing device on another end side;
connecting a cable with the in-body image capturing device and passing the cable through the support tube; and
electrically connecting a control system with the cable.

15. A method of manufacturing an in-body image capturing device, the method comprising:
providing an image capturing unit that includes a lens and an illumination unit, the in-body image capturing device being capable of being introduced into a body;
integrally molding a light-transmitting body and a light shielding body with each other in a casing by fitting, in an interior of a die of a whole of the casing, the light shielding body that has been molded in advance and pouring a transparent resin into gaps in the die, or by, in one molding machine, pouring a black resin into an interior of a die of the light shielding body, hardening the black resin, setting, in a die of a whole of the casing, the black resin thus hardened, and pouring the transparent resin into the die of the whole of the casing; and housing the image capturing unit and the illumination unit in the casing, wherein the light-transmitting body includes an illumination cover portion that covers the illumination unit and a lens cover portion that covers the lens, the light shielding body includes a lens surrounding portion that surrounds the lens, the lens surrounding portion includes a light shielding wall that is positioned between the lens and the illumination unit, and the light shielding wall includes a tip end portion that extends, in a cross-sectional view, in a direction from a position of a light entrance surface of the lens to a position of a light entrance surface of the lens cover portion, the light entrance surface of the lens being a surface via which light enters the lens, and the light entrance surface of the lens cover portion being a surface via which light enters the lens cover portion.

* * * * *